US006610495B1

(12) United States Patent
Watt et al.

(10) Patent No.: US 6,610,495 B1
(45) Date of Patent: Aug. 26, 2003

(54) METHOD FOR DETECTING PROTEINACEOUS INHIBITORS OF PROTEIN-PROTEIN OR DNA-PROTEIN INTERACTIONS

(75) Inventors: Paul M. Watt, Claremont (AU); Ursula R. Kees, Claremont (AU)

(73) Assignee: TVW Telethon Intstitute for Child Health Research, Western Australia (AU)

( * ) Notice: Subject to any disclaimer, the term of this patent is extended or adjusted under 35 U.S.C. 154(b) by 0 days.

(21) Appl. No.: 09/227,652

(22) Filed: Jan. 8, 1999

Related U.S. Application Data
(60) Provisional application No. 60/070,989, filed on Jan. 9, 1998.

(51) Int. Cl.[7] .............................................. G01N 33/53
(52) U.S. Cl. ...................... 435/7.1; 435/7.2; 435/7.21; 435/7.3; 435/7.31; 435/7.32; 435/DIG. 5; 435/DIG. 6; 435/DIG. 7; 435/DIG. 8
(58) Field of Search .................. 435/4, 6, 7.2, 7.31, 435/DIG. 7, 15, 14, 27, 34, 35, 7.1, 7.21, 7.32, DIG. 5, DIG. 6, DIG. 8

(56) References Cited

U.S. PATENT DOCUMENTS

| | | | |
|---|---|---|---|
| 5,695,941 A | * 12/1997 | Brent et al. ...................... 435/6 |
| 5,695,961 A | 12/1997 | Minton et al. | |
| 5,846,722 A | * 12/1998 | Kauvar et al. .................. 435/6 |

FOREIGN PATENT DOCUMENTS

| | | |
|---|---|---|
| WO | WO 94/09133 | 4/1994 |
| WO | WO 94/12221 | 6/1994 |
| WO | WO 95/17412 | 6/1995 |
| WO | WO 95/20652 | 8/1995 |
| WO | WO 95/26400 | 10/1995 |
| WO | WO 95/34646 | 12/1995 |
| WO | WO 96/35203 | 10/1996 |
| WO | WO 98/16835 | 4/1998 |

OTHER PUBLICATIONS

Paul Bartel et al., *Elimination of False Positives That Arise in Using the Two–Hybrid System*, BioTechniques, vol. 14, No. 6, 1993, pp. 920–924.

Heng Hong et al., *GRIP1, a novel mouse protein that serves as a transcriptional coactivator in yeast for the hormone binding domains of steroid receptors*, Natl. Acad. Sci. USA, vol. 93, May 1996, pp. 4948–4952.

Ulrich Putz et al., *A tri–hybrid system for the analysis and detection of RNA–protein interactions*, Nucleic Acids Research, vol. 24, No. 23, 1996, pp. 4838–4840.

K.H. Young, *Yeast Two–Hybid: So Many Interactions, (in) So Little Time . . . .*, Biology of Reproduction, vol. 58, 1998, pp. 302–311.

Jeff Staudingert et al., *Interactions among Vertebrate Helix–Loop–Helix Proteins in Yeast Using the Two–hybrid System*, The Journal of Biological Chemistry, vol. 268, No. 7, Mar. 5, 1993, pp. 4608–1611.

Adam N. Goldfarb et al., *Determinants of Helix–Loop–Helix Dimerization Affinity*, The Journal of Biological Chemistry, vol. 271, No. 5, Feb. 2, 1996, pp. 2683–2688.

Pierre Colas et al., *The Impact of two–hybrid and related methods on biotechnology*, Trends in Biotechnolog vol. 16, No. 8, Aug. 1998, pp. 1–13.

Pierre Colas et al., *Genetic selection of peptide aptamers that recognize and inhibit cyclin–dependent kinase 2*, Letters to Nature, vol. 380, Apr. 1996, pp. 548–550.

Edward J. Licitra et al., *A three–hybrid system for detecting small ligand–protein receptor interactions*, Proc. Natl. Acad. Sci. USA, vol. 93, Nov. 1996, pp. 12817–12821.

Mark A. Osborne et al., *The Yeast Tribrid System—Genetic Detection of trans–phosphorylated ITAM–SH2–Interactions*, Bio/Technology, vol. 13, Dec. 1995, pp. 1474–1478.

Hainzl, T. & Boehm, T. (1994) A versitile expression vector for the in vitro study of protein–protein interactions: characterization of E47 mutant proteins. Oncogene 9:885–891.

Mendelsohn, A.R. & Brent, R. (1994) Applications of interaction traps/two–hybrid systems to biotechnology research. Curr. Opinion Biotechnology 5:482–486.

Pelletier, J.N., et al., (1997) A Protein Complementation Assay for Detection of Protein–Protein Interactions in vivo. Derwent Accession No. XP–002064563.

Zhang, J. & Lautar, S. (1996) A Yeast Three–Hybrid Method to Clone Terany Protein Complex Components. Anal. Biochem. 242:68–72.

* cited by examiner

Primary Examiner—Andrew Wang
Assistant Examiner—Tomas Friend
(74) Attorney, Agent, or Firm—Knobbe, Martens, Olson & Bear, LLP

(57) ABSTRACT

The present invention relates generally to a method of identifying modulators of biological interactions and agents useful for same. More particularly, the present invention contemplates a method of detecting inhibitors of biological interactions involving proteinaceous and/or nucleic acid molecules and more particularly a method of identifying peptide inhibitors of biological interactions having adverse effects on living cells, tissue or organisms. The present invention provides the means by which a wide range of peptide-based therapeutic, prophylactic and diagnostic reagents may be developed.

85 Claims, 2 Drawing Sheets

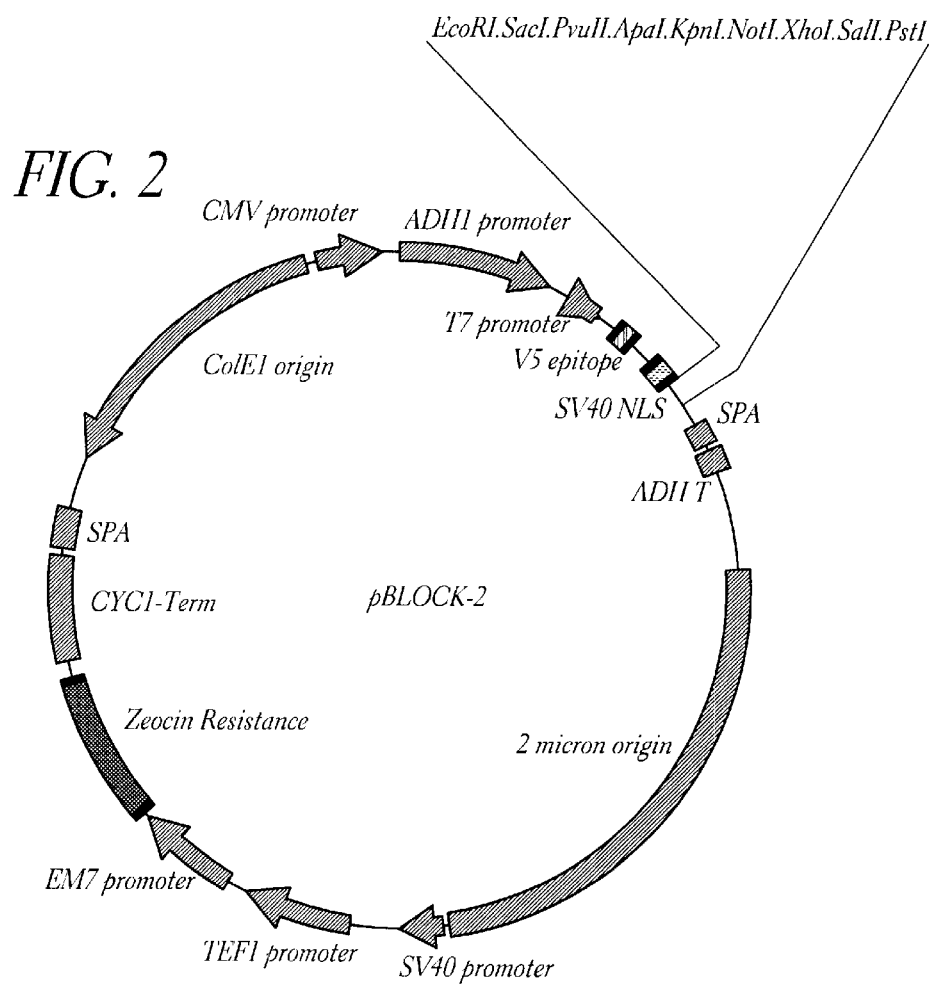

METHOD FOR DETECTING PROTEINACEOUS INHIBITORS OF PROTEIN-PROTEIN OR DNA-PROTEIN INTERACTIONS

RELATED APPLICATION

The present application claims the benefit of priority under 35 U.S.C. §119(e) of Provisional Application No. 60/070,989, filed Jan. 9, 1998.

FIELD OF THE INVENTION

The present invention relates generally to a method of identifying modulators of biological interactions and agents useful for same. More particularly, the present invention contemplates a method of detecting inhibitors of biological interactions involving proteinaceous and/or nucleic acid molecules and more particularly a method of identifying peptide inhibitors of biological interactions having adverse effects on living cells, tissue or organisms. The present invention provides the means by which a wide range of peptide-based therapeutic, prophylactic and diagnostic reagents may be developed.

GENERAL

This specification contains nucleotide and amino acid sequence information prepared using the programme PatentIn Version 2.0, presented herein after the bibliography. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (eg. <400>1 (SEQ ID NO: 1), <400>2 (SEQ ID NO: 2), etc).

Bibliographic details of the publications numerically referred to in this specification are collected at the end of the description. All patents, patent applications, and publications cited herein are incorporated by reference in their entirety.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purposes of exemplification only Functionally-equivalent products, compositions and methods are clearly within the scope of the invention, as described herein.

BACKGROUND TO THE INVENTION

Biological interactions, such as protein:protein interactions, protein:nucleic interactions, protein:ligand interactions and nucleic acid:nucleic acid interactions are involved in a wide variety of processes occurring in living cells. For example, agonism and antagonism of receptors by specific ligands, including drugs, hormones, second messenger molecules, etc. may effect a variety of biological processes such as gene expression, cellular differentiation and growth, enzyme activity, metabolite flow and metabolite partitioning between cellular compartments, amongst others. DNA:protein and RNA:protein interactions are well known for their effects in regulating gene expression in both prokaryotic and eukaryotic cells, in addition to being critical for DNA replication and in the case of certain viruses, RNA replication.

Undesirable or inappropriate gene expression and/or cellular differentiation, cellular growth and metabolism may also be attributable, at least in many cases, to biological interactions involving the binding and/or activity of proteinaceous molecules, such as transcription factors, peptide hormones, receptor molecules and enzymes, amongst others.

In one example, it is known that several genes activated by chromosomal translocations in lymphoid malignancies code for transcription factors, for example MYC, LYL-1 and SCL, which appear to function via protein-protein interactions. In normal cells, these proteins are in an appropriate equilibrium with their interaction partners which is disturbed as a consequence of oncogene activation and is thought to result in transcription of target genes normally expressed in other cells or lineages. These transcription factors may also substitute for, or antagonise, the function of closely related endogenous proteins to perturb gene expression essential for normal growth control.

Peptides present potential therapeutic and prophylactic agents for many human and animal diseases, biochemical disorders and adverse drug effects, because they can interact with other molecules highly specifically. For example, mimetic peptides have been reported to inhibit protein interactions and/or enzymic functions. More specific examples include a nonapeptide derived from the ribonucleotide reductase of herpes simplex virus which is linked to an enterotoxin subunit for delivery into cells via its receptor. The peptide conjugate is found to inhibit herpes simplex type I replication in quiescent Vero cells (Marcello et al. 1994). Using detailed knowledge of the PCNA-interaction domain of $p21^{WAF1}$, a peptide was designed which effectively blocked the interaction. This 20-mer peptide bound with sufficient affinity to block SV40 replication (Warbrick et al. 1996). A 20-mer peptide sequence derived from p16 was found to interact with cdk4 and cdk6 and inhibited pRB phosphorylation and cell cycle progression (Fahraeus 1996). Peptides have even been shown to function as inhibitors in animal models. For examples, a peptide targeting the ICE protease was shown to be a potent protective inhibitor against liver apoptosis induced by TNF-α in the mouse (Rouquet et al. 1996).

A major problem to be overcome in the field of peptide therapeutics and prophylactics is the identification of specific amino acid sequences having a desired antagonist or agonist activity against a particular biological interaction in a particular cellular environment.

Additionally, in view of the wide range of possible applications of peptide therapeutics, the potential number of useful amino acid sequences is enormous. This poses a particular problem in terms of identifying, from the vast pool of potential amino acid sequences having utility, those amino acid sequences which have a specific activity under a particular set of cellular conditions.

There is currently no available method for screening random peptide libraries in vivo for the purpose of identifying specific peptides which inhibit specific protein interactions.

Accordingly, there is a need to develop technologies which provide for the rapid, large-scale determination of useful peptide therapeutics.

SUMMARY OF THE INVENTION

One aspect of the present invention provides a method of identifying a peptide, oligopeptide or polypeptide which is capable of modulating a biological interaction in a host cell said method comprising the steps of:

(i) producing a peptide library in a cellular host wherein the transformed cells of said library contain at least a first nucleotide sequence which comprises or encodes a reporter molecule the expression of which is operably under control of said biological interaction and a second nucleotide sequence which encodes said peptide, oligopeptide or polypeptide placed operably under the control of a suitable promoter sequence;

(ii) culturing said cellular host for a time and under conditions sufficient for expression of said second nucleotide sequence to occur; and (iii) selecting cells wherein expression of said reporter molecule is modified.

A second aspect of the present invention contemplates peptides, oligopeptides and polypeptides identified by the method of the present invention.

Another aspect of the present invention contemplates a pharmaceutical composition comprising a peptide, oligopeptide and polypeptide which is capable of modulating a biological interaction and one or more pharmaceutically acceptable carriers and/or diluents.

Another aspect of the present invention provides a shuttle vector which is capable of expressing a first amino acid sequence as a fusion with a second amino acid sequence in which it is conformationally constrained, wherein said shuttle vector at least comprises:

(i) a first expression cassette comprising:
  (a) a multiple cloning site for insertion of a first nucleotide sequence encoding said first amino acid sequence, wherein said multiple cloning site is adjacent to one or more second nucleotide sequences encoding a nuclear localisation motif and/or polypeptide loop such that a fusion polypeptide is capable of being produced between said first and second amino acid sequences;
  (b) two or more tandem promoter sequences to which said first and second nucleotide sequences are operably connected in use wherein one of said promoter sequences is a bacterially-expressible promoter and wherein one of said promoter sequences is a yeast-expressible promoter; and
  (c) a terminator sequence adjacent to the multiple cloning site and distal to said promoter sequence and second nucleotide sequences;

(ii) a bacterial origin of replication; and (iii) a eukaryotic origin of replication.

In an alternative embodiment, the shuttle vector of the invention further comprises a second expression cassette comprising a selectable marker gene operably linked to two or more promoter sequences and placed upstream of a terminator sequence, wherein one of said promoter sequences is a bacterially-expressible promoter and wherein one of said promoter sequences is a yeast-expressible promoter.

In an alternative embodiment, the subject shuttle vector is further modified to provide for expression in mammalian cells, by introducing into the first and second expression cassettes mammalian cell-expressible promoter and terminator sequences in tandem array with the promoter and terminator sequences already present in the subject expression cassettes.

A further aspect of the invention provides a method of identifying an antagonist of a biological interaction in a bacterial cell, said method comprising:

(i) placing the expression of a reporter molecule operably under the control of a biological interaction in said cell, wherein at least one partner of said biological interaction comprises a peptide, oligopeptide, polypeptide or protein encoded by a nucleotide sequence that is placed operably in is connection with a bacterial-expressible promoter in pBLOCK-1 or a derivative thereof;

(ii) incubating the cell in the presence of a candidate compound to be tested for the ability to antagonise the biological interaction; and (iii) selecting cells wherein expression of said reporter molecule is modified.

BRIEF DESCRIPTION OF THE DRAWINGS

FIG. 2 is a diagrammatic representation of the mammalian/yeast/*E.coli* shuttle vector pBLOCK-2. The pBLOCK-2 vector is identical to the pBLOCK-1 vector except for the presence of the mammalian-expressible CMV and SV40 promoters and the SPA terminator sequences.

DETAILED DESCRIPTION OF THE PREFERRED EMBODIMENTS

Figure 1:
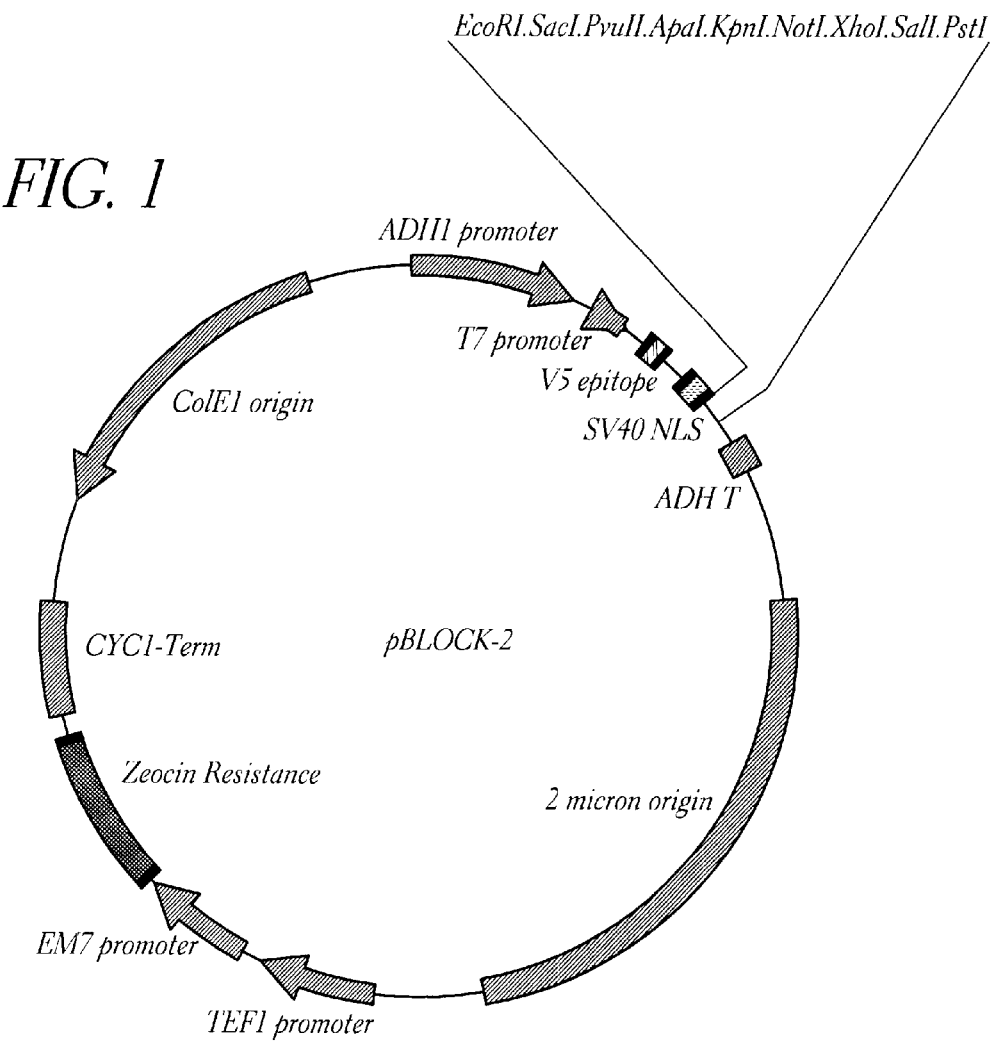
FIG. 1 is a diagrammatic representation of the yeast/*E.coli* shuttle vector pBLOCK-1. Positions of the ADH1, T7, EM7 and TEF1 promoters are indicated. Arrows indicate the direction of transcription. The CYC1 and ADH terminator sequences are indicated by CYC1-term and ADH T, respectively. The EM7 and TEF1 promoters regulate expression of the Zeocin resistance gene, whilst the ADH1 and T7 promoters regulate expression of a nucleic acid molecule inserted into the multiple cloning site (EcoRI . . . PstI) in yeast and bacteria, respectively, wherein said nucleic acid molecule is expressed as a fusion peptide, oligopeptide or polypeptide with the SV40 nuclear localisation signal (SV40 NLS) and the V5 epitope.

In work leading up to the present invention, the inventors sought to develop novel screening methods for identifying potential peptide-based compounds which are capable of modulating biological interactions involving proteins or polypeptides. Using genetic engineering technology, the inventors have developed a cellular gene expression system in which the effect of a peptide-based compound on any specific interaction involving a proteinaceous molecule may be assayed, by coupling protein interaction-dependent gene expression to cellular viability and/or reporter gene expression.

Accordingly, the present invention relates generally to a method of identifying modulators of biological interactions and agents useful for same. More particularly, the present invention contemplates a method of detecting inhibitors of biological interactions involving proteinaceous and/or nucleic acid molecules and more particularly a method of identifying peptide inhibitors of biological interactions having adverse effects on living cells, tissue or organisms. The present invention provides the means by which a wide range of peptide-based therapeutic, prophylactic and diagnostic reagents may be developed.

One aspect of the present invention provides a method of identifying a peptide, oligopeptide or polypeptide which is capable of modulating a biological interaction in a host cell said method comprising the steps of:

(i) producing a peptide library in a cellular host wherein the transformed cells of said library contain at least a first nucleotide sequence which comprises or encodes a reporter molecule the expression of which is operably under control of said biological interaction and a second nucleotide sequence which encodes said peptide, oligopeptide or polypeptide placed operably under the control of a suitable promoter sequence;

(ii) culturing said cellular host for a time and under conditions sufficient for expression of said second nucleotide sequence to occur; and (iii) selecting cells wherein expression of said reporter molecule is modified.

As used herein, the term "biological interaction" shall be taken to refer to a physical association between two or more molecules or "partners", wherein said association is involved in a cellular process or alternatively, is required for said cellular process to occur. The "association" may involve the formation of an induced magnetic field or magnetic field, covalent bond formation such as a disulfide bridge formation between polypeptide molecules, an ionic interaction such as occur in an ionic lattice, a hydrogen bond or alternatively, a van der Waals interaction such as a dipole-dipole interaction, dipole-induced-pole interaction, induced-dipole-induced-dipole interaction or a repulsive interaction or any combination of the above forces of attraction.

Preferably, at least one of the partners in a biological interaction contemplated by the invention is a peptide, polypeptide, protein or enzyme molecule or a modified derivative thereof. According to this embodiment, the remaining partner(s) is(are) a molecule selected from the list comprising nucleic acid such as single-stranded or double-stranded RNA or DNA, a peptide, polypeptide, protein, enzyme, carbohydrate, amino acid, nucleotide, nucleoside, lipid, lipoprotein, vitamin, co-enzyme, receptor molecule, hormone, chemical compound, cyclic AMP, metal ion or second messenger molecule, amongst others.

More preferably, the biological interaction is a protein::protein interaction or a protein:peptide interaction or a protein:polypeptide interaction or involve a higher-order (i.e. tertiary, quaternary, etc) complex of same (e.g. a protein:protein:protein interaction).

In a particularly preferred embodiment, the biological interaction is between a first partner comprising a peptide, polypeptide, protein or enzyme molecule and a second partner, comprising a nucleic acid molecule such as DNA or RNA or alternatively, a peptide, polypeptide or protein or a derivative or analogue thereof.

The biological interaction regulating reporter gene expression may comprise an interaction between two protein or polypeptide partners which is capable of regulating the activity of a non-naturally-occurring promoter, thereby altering expression of the first nucleotide sequence (encoding the reporter molecule) to which said promoter is operably connected.

Accordingly, in an alternative embodiment of the present invention, the subject method comprises the further step of introducing into the cellular host one or more further nucleic acid molecules which encodes one or more polypeptide binding partners which are involved in the biological interaction, placed operably under the control of one or more suitable promoter sequence.

The further nucleic acid molecules may be introduced into the cellular host before or after the peptide library is produced. Any standard means, may be used for their introduction, including cell mating, transformation or transfection procedures.

Preferably, the number of polypeptide binding partners is at least two and these may be expressed from separate DNA molecules or genetic constructs or alternatively, from a single DNA molecule or genetic construct, the only requirements being that both polypeptide binding partners are expressed in any one cell at the same time as the second nucleotide sequence and that said polypeptide binding partners are expressed under conditions and for a time which is sufficient for a productive biological interaction capable of modulating expression of the first nucleotide sequence to occur.

Thus, the non-naturally occurring promoter regulating expression of the reporter gene may comprise a derivative of a naturally-occurring promoter sequence or a synthetic promoter sequence, optionally including LexA operator sequences or GAL4 binding site sequences for use in a modulating protein:protein interactions wherein one of the partners is a protein capable of recognising and binding functionally to said sequence. According to this embodiment, the biological interaction between the partners leads to transcriptional activation of the promoter regulating expression of the first nucleotide sequence, for example by reconstituting a functional transcription factor, thereby leading to expression of the reporter molecule. Pursuant to expression of a peptide, oligopeptide or polypeptide capable of which is capable of modulating this interaction between the partners, for example by dissociating the binding between the partners or by inhibiting formation of the interaction either competitively or non-competitively, expression of the reporter molecule is modified.

Accordingly, the biological interaction may be a simple interaction between a promoter/operator and a transcription factor which is capable of both binding to said promoter/operator and activating reporter gene expression. Alternatively, the biological interaction may be a simple protein:protein interaction which either directly or indirectly modulates gene expression. However, in a preferred embodiment, the biological interaction comprises two interacting polypeptide binding partners and a third nucleic acid partner wherein:

(i) the first of said polypeptide binding partners comprises an amino acid sequence which is capable of binding to said nucleic acid partner and a further amino acid sequence or conformation capable of interacting with said second polypeptide binding partner; and (ii) the second of said polypeptide binding partners comprises an amino acid sequence which is capable of modulating reporter gene expression and a further amino acid sequence or conformation capable of interacting with said first polypeptide binding partner;

and wherein reporter gene expression is enhanced, induced, activated, decreased or repressed when said first, second and third partners associate. In the context of this embodiment, the association between the first and second polypeptide partners reconstitutes a functional and novel transcription factor or alternatively a transcriptional activator or repressor molecule which modulates reporter gene expression when bound to the third partner comprising nucleic acid, which may correspond to an operator sequence or cis-acting element such as a LexA operator (e.g. from ColE1 promoter) or GAL4-DNA binding site (i.e. GAL4 recognition sequence). In this regard, the expressed peptide, oligopeptide or polypeptide may modulate expression which is modulated under control of the biological interaction, by interfering with any component of said biological interaction, for example the protein:protein or protein:nucleic acid binding or even transcriptional activation or repression.

In an exemplification of this embodiment, the first polypeptide partner may comprise a DNA binding domain fusion between the GAL4 DNA or LexA operator binding domain of a transcription factor and an amino acid sequence which is capable of dimerisation with the second polypeptide partner such as a region of the SCL polypeptide capable of interacting with the DRG, E47 or LMO2 proteins, the second polypeptide partner comprises an activation domain fusion between a transcriptional activator domain (e.g. from GAL4) and a region of the DRG, E47 or LMO2 proteins which is capable of interacting with the first polypeptide partner and the third binding partner comprises a non-naturally occurring promoter sequence which includes the GAL4 binding site or LexA operator sequences for "docking" of the DNA binding domain fusion and other sequences as required for modulating reporter gene expression under control of the biological interaction. The DNA binding domain fusion and the activation domain fusion and peptide, oligopeptide or polypeptide are preferably as fusion proteins with a nuclear localisation sequence to facilitate their transport to the site of transcription in a eukaryotic cell (i.e. the nucleus) in particular the SV40 large T antigen nuclear localisation signal.

Preferably, the third binding partner is operably connected to a reporter molecule comprising the URA3 structural gene which, when expressed in the presence of 5-fluororotic acid under control of the biological interaction, will result in reduced cell growth or viability or cell death. In this case, inhibition of the biological interaction by the peptide, oligopeptide or polypeptide will lead to increased cell viability or cell survival in the presence of the 5-fluororotic acid substrate.

Alternatively, the counterselectable reporter gene may be CYH2 which encodes a product which is lethal in the presence of the drug cycloheximide.

Alternatively, the counterselectable marker gene may be LYS2 which confers lethality in the presence of the drug α-aminoadipate (α-AA).

Alternatively, more than one of the above counterselectable reporter genes may be employed concurrently.

The present invention may further be applied to "three hybrid" screening to identify a so-called "adaptor" protein or peptide which is expressed from the second nucleotide sequence, wherein said adaptor protein is required for the interaction between the first and second polypeptide partners to occur. In performing such an embodiment of the invention, the same cell lines (i.e. yeast strains or other cellular host) may be employed as with the "two hybrid" screens described herein. In an exemplification of this embodiment, the peptide library is produced in a yeast cell line carrying a first nucleotide sequence that comprises the LexA or GAL4 operator sequences operably connected to the URA3 reporter gene and capable of expressing any first and second polypeptide binding partners, subject to the proviso that at least one of said first and second polypeptide binding partners is capable of interacting with said LexA or GAL4 operator sequences and that the tertiary complex between the first and second partners and the adaptor forms which is capable of interacting with the third binding partner (i.e. LexA or GAL4) to activate expression of the URA3 reporter gene.

For example, the first polypeptide binding partner may comprise a DNA binding domain fusion between the GAL4 DNA or LexA operator binding domain of a transcription factor and an amino acid sequence that dimerises with the adaptor polypeptide, whilst the second polypeptide binding partner comprises an activation domain fusion between a transcriptional activator domain, such as the GAL4 activator domain, and an amino acid sequence that dimerises with the adaptor protein.

Alternatively, there may be direct interaction between the first and second binding partners, wherein full transcriptional activity occurs only in the presence of the adaptor protein encoded by the second nucleotide sequence.

Those skilled in the art will be aware that the present invention may be modified to identify any of the polypeptide binding partners in either the "two hybrid" or "three hybrid" screening formats described herein.

In the context of the polypeptide identified in performing the present invention, the term "derivative" shall be taken to refer hereinafter to mutants, parts or fragments of a complete polypeptide as defined herein which are functionally equivalent. Derivatives include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are also contemplated by the present invention. Procedures for derivatizing proteins are well-known in the art. "Analogues" of a peptide, protein, polypeptide or enzyme are functionally equivalent molecules which comprise one or more non-naturally occurring amino acid analogues known to those skilled in the art.

In the present context, the terms "host cell" and "cellular host" or similar term refer to prokaryotic and eukaryotic cells capable of supporting the expression of a reporter molecule under the control of a biological interaction, irrespective of whether or not the biological interaction or the reporter molecule is endogenous to the cell.

Those skilled in the art will be aware that a "transformed cell" is a cell into which exogenous nucleic acid has been introduced, wherein the exogenous nucleic acid is either integrated into the host cell genome or alternatively, maintained therein as an extrachromosomal genetic element such as a plasmid, episome or artificial chromosome, amongst others.

The transformed cell of the present invention may be any cell capable of supporting the expression of exogenous DNA, such as a bacterial cell, insect cell, yeast cell, mammalian cell or plant cell. In a particularly preferred embodiment of the invention, the cell is a bacterial cell, mammalian cell or a yeast cell.

In a particularly preferred embodiment of the invention, the cell is a yeast cell, more preferably a yeast cell having the genotype MATα, ura3, trp1, his3, cyh2$^R$, lexAop-URA3, lexAop-CYH2, ade2. Such a yeast strain may be constructed using spontaneous cycloheximide-resistant derivatives of YPH252 (Sikorski et al., 1989) or EGY40 (Golemis and Brent, 1992; Gyuris et al. 1993)

The term "expression" refers at least to the transcription of a nucleotide sequence to produce an RNA molecule. The term "expression may also refer to the combined transcription and translation of a nucleotide sequence to produce a peptide, polypeptide, protein or enzyme molecule or alternatively, to the process of translation of mRNA to produce a peptide, polypeptide, protein or enzyme molecule.

By "operably under control" is meant that a stated first integer is regulated or controlled by a stated second integer.

In the present context, wherein the expression of the reporter molecule is operably under control of a biological interaction, said expression is modified (i.e. enhanced, induced, activated, decreased or repressed) when a peptide, oligopeptide or polypeptide capable of enhancing, inducing, activating, decreasing or repressing the formation of said biological interaction is expressed. Accordingly, it is not usually sufficient for only one partner in the biological interaction to be present for such modified expression of the reporter molecule to occur however, there may be some expression of the reporter molecule in the presence of only one partner.

As used herein, the term "peptide library" is a set of diverse nucleotide sequences encoding a set of amino acid sequences, wherein said nucleotide sequences are preferably contained within a suitable plasmid, cosmid, bacteriophage or virus vector molecule which is suitable for maintenance and/or replication in a cellular host. The term "peptide library" includes a random synthetic peptide library, in which the extent of diversity between the amino acid sequences or nucleotide sequences is numerous, and a limited peptide library in which there is a lesser degree of diversity between said sequences. The term "peptide library" further encompasses random amino acid sequences derived from a cellular source, wherein the amino acid sequences are encoded by a second nucleotide sequence which comprises bacterial genome fragments, yeast genome fragments, insect genome fragments or compact vertebrate genome fragments, amongst others obtained for example by shearing or partial digestion of genomic DNA using restriction endonucleases, amongst other approaches. A "peptide library" further includes cells, virus particles and bacteriophage particles comprising the individual amino acid sequences or nucleotide sequences of the diverse set.

Preferred peptide libraries according to this embodiment of the invention are "representative libraries", comprising a set of amino acid sequences or nucleotide sequences encoding same, which includes all possible combinations of amino acid or nucleotide sequences for a specified length of peptide or nucleic acid molecule, respectively.

The diversity of peptide libraries, in particular those derived from genoric sources, can be increased by means known to those skilled in the art, such as random or other mutagenesis. In one exemplification of this embodiment, peptide libraries derived from the expression of genomic DNA are amplified or propagated in bacterial strains which are defective in the epsilon (ε) subunit of DNA polymerase m (i.e. dnaQ and mutD alleles) and/or are defective in mismatch repair. *Escherichia coli* mutator strains possessing the mutY and/or mutM and/or mutD and/or mutT and/or mutA and/or mutC and/or mutS alleles are particularly useful for such applications. Bacterial strains carrying such mutations are readily available to those skilled in the art and are fully described for example, by Akiyama et al 1989; Fijalkowska and Schaaper, 1995; Frick et al, 1995; Lu et al, 1995; Maki and Sekiguchi, 1992; Miller, 1992; Miller and Michaels, 1996; Moriya and Gollman, 1992; Schaaper and Cornacchio, 1992; Slupska et al, 1996; and Tajiri et al, 1995.

In a particularly preferred embodiment of the invention, the peptide library comprises cells, virus particles or bacteriophage particles comprising a diverse set of nucleotide sequences which encode a diverse set of amino acid sequences, wherein the member of said diverse set of nucleotide sequences are placed operably under the control of a promoter sequence which is capable of directing the expression of said nucleotide sequence in said cell, virus particle or bacteriophage particle.

Accordingly, the peptide, oligopeptide or polypeptide encoded by the second nucleotide sequence may comprise any amino acid sequence of at least about 1 to 60 amino acids in length and may be derived from the expression of nucleotide sequences which are prepared by any one of a variety of methods such as, for example, random synthetic generation. Preferably, the peptide is a 20-mer peptide. The use of larger fragments, particularly employing randomly sheared nucleic acid derived from bacterial, yeast or animal genomes, is not excluded.

Alternatively or in addition, the peptide, oligopeptide or polypeptide is expressed as a fusion protein with a nuclear targeting motif capable of facilitating targeting of said peptide to the nucleus of said host cell where transcription occurs, in particular the yeast-operable SV40 nuclear localisation signal.

Alternatively, or in addition, the peptide, oligopeptide or polypeptide may be expressed as a fusion protein with a peptide sequence capable of enhancing, increasing or assisting penetration or uptake of the peptide by an isolated cell such as when the subject peptide, oligopeptide or polypeptide is synthesized ex vivo and added to isolated cells in culture. In a particularly preferred embodiment, the peptide sequence capable of enhancing, increasing or assisting penetration or uptake is functional in insect cells or mammalian cells, for example the Drosophila penetratin targeting sequence, amongst others. According to this embodiment, the fusion protein at least comprises the following amino acid sequence set forth in <400>4 (SEQ ID NO: 4):

CysArgGlnIleLysIleTrpPheGlnAsnArgArgMetLysTrp-LysLys (Xaa)$_n$Cys

Cys (penetratin 16mer, SEQ ID NO: 4)(Xaa)$_n$Cys.
or a homologue, derivative or analogue thereof, wherein Xaa is any amino acid residue and n has a value greater than or equal to 1. Preferably, the value of n will be at least 5, more preferably between about 5 and about 20, even more preferably between about 15 and about 35 and still even more preferably between about 30 and about 50 and still more preferably between about 35 and about 55. In a still more preferred embodiment, the value of n is between at least about 40 and at least about 60.

The peptide, oligopeptide or polypeptide may also be expressed in a conformationally constrained or conformationally unconstrained form. Amino acid sequences which are expressed in a conformationally constrained form may be expressed within a second polypeptide as a fusion protein such that they are effectively "nested" in the secondary structure of the second polypeptide. Alternatively, the peptide, oligopeptide or polypeptide may be circularised by means of oxidising flanking cysteine residues, to limit conformational diversity. This may be particularly beneficial where the amino acid sequences are nested within a surface-exposed or functional site of a protein, such that they are accessible to the biological interaction of interest. For example, the peptide, oligopeptides or polypeptides may be expressed within a thioredoxin (Trx) polypeptide loop. Whilst not being bound by any theory or mode of action, expression of the peptides, oligopeptides or polypeptides in a conformationally constrained form limits the degrees of freedom and the entropic cost associated with its binding, imparting a high degree of affinity and specificity to the interaction.

Reference herein to a "promoter" is to be taken in its broadest context and includes the transcriptional regulatory sequences of a classical genoric gene, including the TATA box which is required for accurate transcription initiation in eukaryotic cells, with or without a CCAAT box sequence and additional regulatory elements (i.e. upstream activating sequences, enhancers and silencers). Promoters may also be lacking a TATA box motif, however comprise one or more "initiator elements" or, as in the case of yeast-derived promoter sequences, comprise one or more "upstream activator sequences" or "UAS" elements. For expression in prokaryotic cells such as bacteria, the promoter should at least contain the −35 box and −10 box sequences.

A promoter is usually, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of the subject reporter molecule in a cell. Preferred promoters may contain additional copies of one or more specific regulatory elements, to further enhance expression of the gene and/or to alter the spatial expression and/or temporal expression. For example, regulatory elements which confer copper inducibility may be placed adjacent to a heterologous promoter sequence driving expression of the reporter, thereby conferring copper inducibility on the expression of said gene.

Placing a gene operably under the control of a promoter sequence means positioning the said gene such that its expression is controlled by the promoter sequence. Promoters are generally positioned 5' (upstream) to the genes that they control. In the construction of heterologous promoter/ structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in regulating the expression of the reporter molecule and/or peptide, oligopeptide or polypeptide and/or the polypeptide binding partner in a cell include viral, fungal, yeast, insect, animal and plant derived promoters. Preferred promoters are capable of conferring expression in a eukaryotic cell, especially a yeast or mammalian cell. The promoter may regulate the expression of a gene constitutively, or differentially with respect to the tissue in which expression occurs or, with respect to the developmental stage at which expression occurs, or in response to external stimuli such as environmental stress, or hormones amongst others.

Particularly preferred promoters according to the present invention include those naturally-occurring and synthetic promoters which contain binding sites for transcription factors, more preferably for helix-loop-helix (HLH) transcription factors, zinc finger proteins, leucine zipper proteins and the like. Preferred promoters may also be synthetic sequences comprising one or more upstream operator sequences such as LexA operator sequences or activating sequences derived from any of the promoters referred to herein such as GAL4 DNA binding sites.

Those skilled in the art will recognise that the choice of promoter will depend upon the nature of the cell being transformed and the molecule to be expressed. Such persons will be readily capable of determining functional combinations of minimum promoter sequences and operators for cell types in which the inventive method is performed.

Whilst the invention is preferably performed in yeast cells, the inventors clearly contemplate modifications wherein the invention is performed entirely in bacterial or mammalian cells, utilising appropriate promoters which are operable therein to drive expression of the various assay components, in combination with a counter selective reporter gene operable in such cells. Such embodiments are within the ken of those skilled in the art.

In a particularly preferred embodiment, the promoter is a yeast promoter, mammalian promoter, a bacterial or bacteriophage promoter sequence selected from the list comprising GAL1, CUP1, PGK1, ADH2, PHO5, PRB1, GUT1, SPO13, ADH1, CMV, SV40 or T7 promoter sequences. The invention further provides for the screening of blockers isolated from a yeast reverse two hybrid screen, in mammalian bioassays, toxicity and/or growth assays in subsequent screens ex vivo using shuttle vectors capable of functioning in yeast and mammalian cells.

For expression in mammalian cells, it is preferred that the promoter is the CMV promoter sequence, more preferably the CMV-IE promoter or alternatively, the SV40 promoter and, in particular the SV40 late promoter sequence. These, and other promoter sequences suitable for expression of genes in mammalian cells are well-known in the art.

Examples of mammalian cells contemplated herein to be suitable for expression include COS, VERO, HeLa, mouse C127, Chinese hamster ovary (CHO), WI-38, baby hamster kidney (BHK) or MDCK cell lines, amongst others. Such cell lines are readily available to those skilled in the art.

The prerequisite for producing intact polypeptides in bacterial cells and, in particular, in *Escherichia coli* cells, is the use of a strong promoter with an effective ribosome binding site, such as a Shine-Dalgarno sequence, which may be incorporated into expression vectors carrying the first and second nucleotide sequences, or other genetic constructs used in performing the various alternative embodiments of the invention. Typical promoters suitable for expression in bacterial cells such as *E. coli* include, but are not limited to, the lacz promoter, temperature-sensitive $\lambda_L$ or $\lambda_R$ promoters, T7 promoter or the IPTG-inducible tac promoter A number of other vector systems for expressing the nucleic acid molecule of the invention in *E. coli* are well-known in the art and are described for example in Ausubel et al (1987) or Sambrook et al (1989). Nunerous sources of genetic sequences suitable for expression in bacteria are also publicly available in various plasmid constructs, such as for example, pKC30 ($\lambda_L$:Shimatake and Rosenberg, 1981), pKK173-3 (tac: Amann and Brosius, 1985), pET-3 (T7: Studier and Moffat, 1986) or the pQE series of expression vectors (Qiagen, Calif.), amongst others.

Suitable prokaryotic cells for expression include corynebacterium, salmonella, *Escherichia coli*, Bacillus sp. and Pseudomonas sp, amongst others. Bacterial strains which are suitable for the present purpose are well-known in the relevant art (Ausubel et al, 1987; Sambrook et al, 1989).

Wherein the promoter is intended to regulate expression of the reporter molecule, it is particularly preferred that said promoter include one or more recognition sequences for the binding of a DNA binding domain derived from a transcription factor, for example a GAL4 binding site or LexA operator sequence.

As used herein, the term "reporter molecule" shall be taken to refer to any molecule which is capable of producing an identifiable or detectable result.

In one embodiment of the invention, the reporter molecule is an enzyme, peptide, oligopeptide or polypeptide which comprises a visible product or at least, when incubated in the presence of a substrate molecule can convert said substrate to a visible product, such that cells expressing the reporter molecule may be readily detected. For example, the expression of reporter genes that encode polypeptides, which themselves fluoresce, or cause fluorescence of a second molecule, can be operably connected to the biological interaction being assayed, to facilitate the detection of cells wherein expression of the reporter molecule is present or absent. Such applications are particularly useful in high through-put drug screening approaches, wherein it is desirable to rapidly screen a large number of drug candidates for their agonist/antagonist properties with respect to the biological interaction in question. Preferred reporter molecules according to this embodiment include, but are not limited to the *Escherichia coli* β-galactosidase enzyme, the firefly luciferase protein (Ow et al, 1986; Thompson et al, 1991) and the green fluorescent protein (Prasher et al, 1992; Chalfie et al, 1994; Inouye and Tsuji, 1994; Cormack et al, 1996; Haas et al, 1996; see also GenBank Accession No. U55762). Persons skilled in the art will be aware of how to utilise genetic sequences encoding such reporter molecules in performing the invention described herein, without undue experimentation. For example, the coding sequence of the gene encoding such a reporter molecule may be modified for use in the cell line of interest (e.g. human cells, yeast cells) in accordance with known codon usage preferences. Additionally the translational efficiency of mRNA derived from non-eukaryotic sources may be improved by mutating the corresponding gene sequence or otherwise introducing to said gene sequence a Kozak consensus translation initiation site (Kozak, 1987).

Particularly preferred reporter molecules according to the present invention are those which produce altered cell growth or viability, including the ability to induce cell death. In the present context, the reporter molecule either comprises the first nucleic acid molecule or is encoded by said first nucleic acid molecule. Accordingly, those skilled in the art will be aware that the reporter molecule of such an embodiment is preferably a peptide, polypeptide, enzyme, abzyme or other protein molecule or alternatively, an isolated nucleic acid molecule.

Preferably, the reporter molecule of the invention is capable of directly or indirectly inhibiting, enhancing or otherwise modulating the growth and/or viability of the host cell. Direct modulation of cell growth and/or viability is where expression of the reporter molecule has a direct consequence on cell growth and/or viability. Indirect modulation of cell growth and/or viability is where expression of the reporter molecule has no direct consequence on cell growth and/or viability, however said expression may modulate cell growth and/or viability when cells are cultured in the presence of a suitable co-factor or substrate molecule, amongst others.

Wherein the reporter molecule is a peptide, polypeptide, enzyme, abzyme or other protein molecule which comprises a cytostatic compound, anti-mitotic compound, toxin, mitogen or growth regulatory substance such as a hormone or protein which is essential to cell growth or viability, it may have a direct effect on cell growth or viability when expressed therein. Similarly, a reporter molecule which comprises a nucleic acid molecule may have a direct effect on cell growth and/or viability, for example wherein the reporter molecule is a ribozyme, antisense molecule, minizyme, or co-suppression molecule which is targeted to the expression of a gene which is capable of modifying cell growth and/or viability.

Wherein it is desirable for the reporter molecule to have an indirect effect on cell growth and/or viability, this may be achieved, for example by coupling expression of the reporter molecule to the production of a cytostatic compound, anti-mitotic compound, toxin or negative growth regulatory molecule.

Accordingly, in a further embodiment, the reporter molecule is an enzyme which, when expressed in the host cell, catalyzes the conversion of a substrate molecule which is not capable of altering or affecting cell growth and/or viability, to produce a product which comprises a toxin, cytostatic compound or anti-mitotic compound. According to this embodiment, the expression of the reporter molecule in the presence of said substrate leads to production of a sufficiently high concentration of the toxin, cytostatic compound or anti-mitotic compound to reduce cell growth or result in cell death.

In a further embodiment, the reporter molecule is an enzyme which, when expressed in the host cell, catalyzes the conversion of a cytostatic or anti-mitotic substrate molecule to produce a product which is incapable of modifying cell growth and/or viability. According to this embodiment, cells incubated in the presence of the substrate molecule do not grow or divide as rapidly as cells which are not incubated therewith. Wherein cells incubated in the presence of the cytostatic or anti-mitotic substrate molecule express the reporter molecule, cell division and/or cell growth is resumed when the concentration of said substrate in said cell is reduced.

In an alternative embodiment, the reporter molecule directly or indirectly enhances cell growth and/or viability, for example by coupling expression of the reporter molecule to the production of a mitogen or positive growth regulatory molecule.

In a further embodiment, the reporter molecule is an enzyme which, when expressed in the host cell, catalyzes the conversion of a first compound which is inactive in modulating cell growth and/or viability to produce a mitogen or positive growth regulatory molecule product. According to this embodiment, cells incubated in the presence of the substrate molecule grow and divide at a normal rate compared to other cells. Expression of the enzyme reporter molecule in the presence of the substrate molecule leads to enhanced cell growth and/or cell division as the concentration of the mitogen or positive growth regulatory molecule is increased in the cell. As a consequence, cells in which the reporter molecule is enhanced as a result of the biological interaction grow and/or divide more rapidly than the surrounding cells in the library, facilitating their detection.

In the context of the present invention, the peptide, oligopeptide or polypeptide identified using the inventive method is capable of modulating the expression of the reporter molecule. Accordingly, the peptide, oligopeptide or polypeptide may be an agonist or an antagonist of the biological interaction under which expression of the reporter molecule is operably placed. Wherein the peptide, oligopeptide or polypeptide is an agonist molecule, reporter molecule expression will be increased or enhanced or activated and, depending upon whether or not the reporter molecule directly or indirectly increases or reduces cell growth and/or viability, cell growth will be increased or reduced, respectively. In such embodiments of the invention however, it is clearly undesirable for the reporter molecule to result in cell death, because it would not be possible to recover the cells expressing the desired peptide. Wherein the peptide, oligopeptide or polypeptide is an antagonist of the biological interaction, reporter molecule expression will be decreased or repressed or inactivated and, depending upon whether or not the reporter molecule directly or indirectly increases or reduces cell growth and/or viability, cell growth will be reduced or increased, respectively. Wherein the reporter molecule leads directly or indirectly to cell death, antagonism of the biological interaction by the antagonist peptide, oligopeptide or polypeptide facilitates survival of the cell compared to cells which do not express the antagonist but express the reporter molecule.

Examples of suitable reporter genes include but are not limited to HIS3 [Larson, R. C. et al. (1996), Condorelli, G. L. et al. (1996), Hsu, H. L., et al. (1991), Osada, et al. (1995)] and LEU2 (Mahajan, M. A. et al., 1996) the protein products of which allow cells expressing these reporter genes to survive on appropriate cell culture medium. Conversely, the reporter gene is the URA3 gene, wherein URA3 expression is toxic to a cell expressing this gene, in the presence of the drug 5-fluoro-orotic acid (5FOA). Other counterselectable reporter genes include CYH2 and LYS2, which confer lethality in the presence of the drugs cycloheximide and α-aminoadipate (α-AA), respectively.

Standard methods are used to introduce the first and second nucleotide sequences into the cellular host. In the case of yeast cells, this may be achieved by mass-mating or transformation.

In one embodiment, the first and second nucleotide sequences are each contained within a separate genetic construct, further comprising a selectable marker gene to facilitate detection of transformed cells, for example an antibiotic resistance selectable marker gene. Preferably, the selectable marker genes for each genetic construct are different, such that the presence of one or both genetic constructs in a single cell may be facilitated. The first and second nucleotide sequences may thus be introduced into the cellular host by shotgun cotransformation and selection on an appropriate media to select for the presence of both selectable marker genes.

Alternatively, the first and second nucleic acid sequences may be introduced by sequential transformation, accompanied by selection for the appropriate marker genes after each transformation event.

Alternatively, the first and second nucleotide sequences may be introduced into separate populations of host cells which are subsequently mated and those cell populations containing both nucleotide sequences are selected on media permitting growth of host cells successfully transformed with both first and second nucleic acid molecules.

Alternatively, the first and second nucleotide sequences may be contained on a single genetic construct and introduced into the host cell population in a single step. In such an embodiment of the invention, the random peptide library is usually produced using a vector which at least comprises the first nucleotide sequence placed operably under control of a suitable promoter with or without operator sequence, and a selectable marker gene, the insertion site for the second nucleotide sequence being selected such that the inserted second nucleotide sequence is capable of being expressed.

These embodiments are in addition to the steps to be performed in relation to the introduction of one or more further nucleic acid molecules which encode one or more polypeptide binding partners of the biological interaction, variations of which are described supra.

The selected host cells can be screened on media comprising the components required to utilise the counter-selectable reporter molecule. Host cells expressing a peptide which inhibits the biological interaction are unable to adequately transcribe the counter-selectable reporter gene thereby permitting the host cell to live in the selection medium. Those host cells expressing peptides, oligopeptides or polypeptides which are unable to inhibit the biological interaction transcribe the reporter gene thereby resulting in the formation of a product which is toxic to the host cell in the presence of the selection medium.

The genetic construct may be in the form of an autonomously replicating vector or may comprise genetic sequences to facilitate integration into a host cell genome.

Alternatively, the first nucleotide sequence encoding the reporter molecule can be integrated into the chromosome of the host cell by homologous recombination of the products of polymerase chain reaction (PCR), or of sequences on another DNA molecule which is incapable of replicating autonomously in yeast cells.

According to the nature of the biological interaction of interest, the first nucleotide sequence may be placed operably in connection with any promoter sequence, the only requirement being that the promoter is capable of regulating gene expression in the host cell selected. Usually, the host cell will be varied to suit the promoter sequence. The present invention clearly extends to the isolation of peptides capable of modulating any biological interaction.

In fact, the present invention will facilitate the identification and isolation of a peptide, oligopeptide or polypeptide which modulates expression of the reporter molecule by agonising or antagonising any regulatory step which is required for expression to occur, not merely steps later in the signal transduction pathway, such as DNA-protein interactions or interactions between transcription factors. Wherein it is desired to isolate a specific amino acid sequence which is capable of modulating a particular biological interaction, it is necessary only to operably connect expression of the first nucleotide sequence to the biological interaction of interest. This is done by placing the first nucleotide sequence operably in connection with a promoter sequence which is regulated by the biological interaction or alternatively, genetically manipulating a promoter sequence which is operably connected to the first nucleic acid molecule thereby placing the promoter under operable control of the biological interaction.

In the case of peptides, oligopeptides or polypeptides which modulate a protein:DNA interaction which is required for gene expression or the modulation of gene expression, for example to isolate a peptide molecule which interacts directly with a cis-acting enhancer or silencer element or a protein to which said element binds, this objective may be achieved by introducing the cis-acting element into a promoter sequence to which the first nucleotide sequence is operably connected. By this means, expression of the reporter molecule is placed operably under the control of the cis-acting element and modulation of gene expression will occur when the appropriate protein molecule either binds to the cis-acting DNA element or to the protein which recognises said element.

In the case of a protein:protein interaction controlling gene expression, the promoter controlling the expression of the first nucleic acid molecule is selected such that it contains the necessary cis-acting elements to which at least one of the proteins involved in the interaction binds. Where there is not complete knowledge of the cis-acting sequences or trans-acting factors involved in regulating gene expression, but the promoter sequence and cell-type in which expression occurs are known, the first nucleotide sequence may be placed operably in connection with that promoter sequence and the resulting nucleic acid molecule introduced into that cell type. Such a relationship forms the basis of "two hybrid" or "three hybrid" screening approaches (see Allen et al., 1995 for review). Wherein the peptide of interest antagonises or agonises any step required for expression or the activation, repression or enhancement of gene expression, the effect will be identified by recording altered expression of the reporter molecule.

By way of exemplification only and without limiting the present invention, the inventors have shown that the present invention successfully detects peptides capable of modulating the expression of the URA3 and/or CYH2 or LYS2 gene placed operably in connection with a promoter which is capable of being artificially regulated by the biological interaction in question, particularly in yeast cells. In the case of LexA-based assays, the promoter regulating expression of the reporter gene will comprise one or more LexA operator sequences, whilst in the case of GAL4-based assays, the promoter will comprise one or more GAL4 binding sites. Thus, the interacting proteins may or may not be transcription-factors, however, by virtue of the present invention they function as yeast transcription factors upon association with one another.

The present invention further contemplates the detection of peptides, oligopeptides and polypeptides which modulate a biological interaction, in a mammalian cell, wherein expression of the counter-selectable reporter gene is placed operably under the control of a mammalian-expressible promoter sequence, which is aberrantly active in the pathogenic situation, for example an oncogene promoter such as MYC. Activity of such a promoter would be blocked directly in cells express a peptide, oligopeptide or peptide capable of inhibiting the oncogene promoter in a mammalian cell.

A preferred embodiment of the invention provides a method of identifying a peptide, oligopeptide or polypeptide which is capable of antagonising a protein:protein interaction in a host cell said method comprising the steps of:

(i) producing a peptide library in a cellular host wherein the transformed cells of said library contain at least a first nucleotide sequence which comprises or encodes a reporter molecule capable of reducing the growth and/or viability of said host cell, the expression of which is operably under control of said protein:protein interaction and a second nucleotide sequence which encodes said peptide, oligopeptide or polypeptide placed operably under control of a promoter sequence;

(ii) culturing said cellular host for a time and under conditions sufficient for expression of said second nucleotide sequence to occur; and (iii) selecting cells wherein expression of said reporter molecule is antagonised, repressed or reduced.

Preferably, the subject method includes the additional first step or later step of introducing into the cellular host one or more further nucleic acid molecules which encode one or more polypeptide binding partners which are involved in the biological interaction, operably under the control of one or more promoter sequences. Such embodiments are described in detail supra.

According to these embodiments of the invention, it is preferred that the reporter molecule comprise a peptide, polypeptide, enzyme, or other protein molecule which is capable of converting an innocuous substrate molecule into a cytostatic compound, anti-mitotic compound or a toxin, such that antagonised expression of the reporter molecule by the subject peptide prevents cell death or at least prevents a reduction in cell growth and/or viability in the presence of the substrate.

More preferably, the reporter gene is URA3 and/or CYH2, amongst others such as LYS2.

In a particularly preferred embodiment, the reporter molecule is the product of the URA3 gene which, when expressed converts 5-fluoroorotic acid (5-FOA) to a toxic product.

One exemplification of this embodiment takes advantage of the fact that most active eukaryotic transcription activators are modular and comprise a DNA binding domain and a DNA activation domain, wherein the DNA binding domain and the DNA activation domain may be contained on the same protein molecule or alternatively, on separate molecules which interact to regulate gene expression. According to this embodiment, the expression of the reporter molecule is placed operably under the control of a protein:protein interaction, for example between the oncogenic proteins SCL and LMO2 which bind to form an active artificial transcription factor. The transcription of the reporter gene can therefore be used as an indicator of two proteins interacting where one of said proteins of interest comprises at least a DNA binding domain and binds to an operator promoter element upstream of the reporter gene and said other protein of interest comprises at least a DNA activation domain. Binding of the DNA binding protein to the operator, in the presence of a function activation domain, initiates transcription of the reporter gene. The URA3 reporter thereby acts as a counter selectable marker.

This embodiment of the invention may be adapted to the identification of amino acid sequences which modulate other protein:protein interactions, by functionally replacing the DNA binding domain of a transcription factor with a different DNA binding domain which is specific for a different cis-acting element in the promoter regulating expression of the reporter molecule. Methods for the production of such fusion proteins are well-known to those skilled in the art. In such cases, the selection of an appropriate DNA binding domain will depend on the nature of the DNA binding site located upstream of the reporter gene.

For example, fusion proteins may be constructed between an oncoprotein and a DNA binding domain and/or a DNA activation domain. For example, a sequence of nucleotides encoding or complementary to a sequence of nucleotides encoding residues 176 to 331 of SCL may be fused to the LexA DNA binding domain and a nucleotide sequence encoding LMO2 may be fused to a DNA activation domain (or vice-versa). Alternatively, a nucleotide sequence encoding HOX11 may be operably linked to the LexA DNA binding domain and a nucleotide sequence encoding a HOX11 binding protein may be operably linked to a DNA binding protein (or vice versa).

The present invention is also particularly useful for identifying peptides, oligopeptides or polypeptides which inhibit protein:protein interactions which normally produce deleterious effects (apart from the deleterious effect of certain reporter molecules), for example interactions involving oncogene products. Specific examples of oncogenes, the products of which form transcription factors contributing to tumorigenesis, include SCL and any one or more of DRG, E47 and/or LMO2.

A further alternative embodiment of the invention provides a method of identifying a peptide, oligopeptide or polypeptide which is capable of modifying a protein:protein interaction in a host cell, said method comprising the steps of:

(i) introducing into said host cell one or more nucleic acid molecules which comprise at least:

(a) a first isolated nucleotide sequence which encodes a reporter molecule wherein said nucleotide sequence is operably connected to an operator sequence or transcription factor binding site;

(b) a second nucleotide sequence which encodes said peptide, oligopeptide or polypeptide or derivative thereof; and (c) one or more further third nucleotide sequences which encode one or more polypeptides, proteins or fusion proteins wherein at least one of said polypeptides, proteins or fusion proteins includes at least one DNA binding domain capable of binding to said operator sequence or transcription factor binding site and at least one of said polypeptides, proteins or fusion proteins includes at least one DNA activation domain or derivative thereof capable of activating the expression of said first nucleotide sequence when targeted to the promoter/operator by interaction with another protein bearing the cognate DNA binding domain;

(ii) culturing said host cell for a time and under conditions sufficient to permit expression of said second and further nucleotide sequences to occur; and (iii) selecting cells wherein expression of said reporter molecule is activated, inhibited or otherwise modified.

The proteins involved in the biological interaction of interest, which are encoded by the second nucleic acid molecule, are synthesised in the host cell, either encoded by one or more foreign nucleotide sequences transformed into the host cell or integrated into the genome of said cell. However, the present invention clearly extends to situations in which these sequences are also encoded by endogenous host cell genes.

According to this embodiment of the invention, the DNA binding domain binds to the operator sequence and, in the presence of the DNA activating region, expression of the reporter molecule occurs. Wherein the second nucleotide sequence encodes a peptide which antagonises or inhibits DNA binding and/or DNA activation, expression of the reporter molecule is repressed, reduced or otherwise inhibited. Alternatively, wherein the second nucleotide sequence encodes a peptide, oligopeptide or polypeptide which agonises or enhances DNA binding and/or DNA activation, expression of the reporter molecule is activated, enhanced or otherwise increased.

Those skilled in the art will recognise that the DNA binding domain and the DNA activation domain may be contained on a single amino acid molecule or alternatively, they may be contained in separate amino acid molecules which interact with each other to regulate reporter gene expression.

Similarly, the first and/or second and/or further nucleotide sequences may be contained on a single nucleic acid molecule, for example in one genetic construct or alternatively, one, two, three or more of said sequences may be contained on separate nucleic acid molecules. Wherein one or more of the nucleotide sequences are contained on separate nucleic acid molecules, then each such nucleotide sequence is further preferably operably connected to its own promoter sequence. Alternatively, where any two or more of the nucleotide sequences are contained on the same nucleic acid molecules, the nucleotide sequences may be expressed under the control of a single promoter or alternatively, under the control of separate promoter sequences.

Those skilled in the art will recognise that the alternatives described supra are equally applicable to this embodiment of the invention.

A particularly preferred embodiment of the present invention contemplates a method of identifying a peptide, oligopeptide or polypeptide which is capable of inhibiting a protein:protein interaction, said method comprising the steps:

(i) introducing into a eukaryotic cell one or more nucleic acid molecules which comprise at least:

(a) a first isolated nucleotide sequence which encodes URA3 or a derivative thereof, operably linked to a LexA operator sequence or GAL4 binding site;

(b) a second nucleotide sequence which encodes a fusion peptide, oligopeptide or polypeptide between a random peptide sequence and a nuclear targeting sequence; and (c) one or more further nucleotide sequences which encode one or more polypeptides, proteins or fusion proteins wherein at least one of said polypeptides, proteins or fusion proteins includes at least one DNA binding domain capable of binding to said operator sequence or binding site and at least one of said polypeptides, proteins or fusion proteins includes at least one DNA activation domain or derivative thereof capable of activating the expression of said first nucleotide sequence and wherein each of said polypeptides, proteins or fusion protein includes a nuclear targeting sequence;

(ii) culturing said host cell for a time and under conditions sufficient to permit expression of said second and further nucleotide sequences to occur; and (iii) selecting cells which grow on media containing 5-FOA.

Optionally, the second nucleotide sequences may further encode cysteine residues flanking said random peptide sequence (e.g. NLS-Cys-(Xaa)$_n$-Cys) or alternatively or in addition, encode a polypeptide a loop in which said random peptide sequence is conformationally constrained, to limit the degree of conformational freedom which said peptide may undergo when expressed in a cell.

Preferably, the eukaryotic cell is a yeast cell.

Preferably, the nuclear targeting sequence is the SV40 nuclear localisation signal. More preferably, the further nucleotide sequence(s) further includes a nucleotide sequence which encodes the thioredoxin (Trx) polypeptide loop and even still more preferably, the fusion peptide is expressed such that it is conformationally constrained by the Trx polypeptide loop.

In a further preferred embodiment, the subject method further comprises the step of isolating the third nucleic acid molecule from the host cell and sequencing the nucleic acid molecule and deriving the amino acid sequence encoded therefor. Synthetic peptides may be produced, based upon the derived amino acid sequence thus obtained. Techniques for such methods are described, for example by Ausubel et al (1987 et seq), amongst others.

Those skilled in the art are well versed in such techniques.

Accordingly, a second aspect of the present invention contemplates peptides, oligopeptides and polypeptides identified by the method of the present invention.

Preferably the peptides, oligopeptides and polypeptides are agonists or antagonists of protein:protein or protein:DNA interactions. More preferably, the peptides, oligopeptides and polypeptides of the present invention are antagonists of protein:protein interactions or protein:DNA interactions and even more preferably, antagonists of protein:protein interactions.

In a particularly preferred embodiment, the peptides of the invention antagonise or inhibit interactions which produce deleterious effects in eukaryotic cells, in particular human or animal cells. More preferably, the peptides, oligopeptides and polypeptides of the invention antagonist or inhibit interactions which involve one or more oncoproteins.

The present invention clearly contemplates the use of said peptides, oligopeptides and polypeptides or fragments or derivatives thereof in the prophylactic or therapeutic treatment of humans or animals. Methods of treatment include their use in peptide therapy regimens such as in the treatment protocols for patients with leukaemia and/or solid tumours. Their use in treatment protocols for said patients includes their administration as a means of blocking further cell division of the malignant cells, for example, targeting of the SCL oncoprotein to arrest the malignant cell division of the patient. The specific targeting of oncoproteins with pharmaceuticals comprising said peptides will reduce the side effects experienced by patients as compared to those experienced with conventional, chemotherapy.

Methods of treatment also include other disorders resulting from deleterious expression of aberrant biological molecules which interfere with normal cellular functions.

Accordingly, another aspect of the present invention contemplates a pharmaceutical composition comprising a peptide, oligopeptide and polypeptide which is capable of modulating a biological interaction and one or more pharmaceutically acceptable carriers and/or diluents.

A preferred embodiment contemplates a pharmaceutical composition wherein said peptide, oligopeptide and polypeptide antagonises a biological interaction having adverse consequences on cell growth and/or viability, such as an oncoprotein interaction, and one or more pharmaceutically acceptable carriers and/or diluents. These components are referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that a dosage unit form contains between about 0.1 25 ug and 20 g of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of inhibiting such deleterious biological interactions. The vector may, for example, be a viral vector.

Another aspect of the present invention provides a shuttle vector which is capable of expressing a first amino acid sequence as a fusion with a second amino acid sequence in which it is conformationally constrained, wherein said shuttle vector at least comprises:

(i) a first expression cassette comprising:
 (a) a multiple cloning site for insertion of a first nucleotide sequence encoding said first amino acid sequence, wherein said multiple cloning site is adjacent to one or more second nucleotide sequences encoding a nuclear localisation motif and/or polypeptide loop such that a fusion polypeptide is capable of being produced between said first and second amino acid sequences;
 (b) two or more tandem promoter sequences to which said first and second nucleotide sequences are operably connected in use wherein one of said promoter sequences is a bacterially-expressible promoter and wherein one of said promoter sequences is a yeast-expressible promoter; and
 (c) a terminator sequence adjacent to the multiple cloning site and distal to said promoter sequence and second nucleotide sequences;
(ii) a bacterial origin of replication; and
(iii) a eukaryotic origin of replication.

In an alternative embodiment, the shuttle vector of the invention further comprises a second expression cassette comprising a selectable marker gene operably linked to two or more promoter sequences and placed upstream of a terminator sequence, wherein one of said promoter sequences is a bacterially-expressible promoter and wherein one of said promoter sequences is a yeast-expressible promoter.

In a particularly preferred embodiment, the bacterial origin of replication is the ColE1 origin and the eukaryotic origin of replication is operable at least in a yeast cell and more preferably comprises the 2 micron (2 $\mu$m) origin of replication.

Preferably, the selectable marker gene is the zeocin resistance gene (Zeocin is a drug of the bleomycin family which is trademark of InVitrogen Corporation). An alternative selectable marker gene is AURI-C which confers resistance to the antibiotic aureobasidin A. Those skilled in the art will be aware of other selectable marker genes useful in the performance of the present invention and the subject invention is not limited by the nature of the selectable marker gene.

The bacterially-expressible promoter may be any promoter which is capable of regulating expression of a gene at least in a bacterial cell, preferably an *Escherichia coli* cell. Examples of suitable bacterially-expressible promoters include the T3 promoter, SP6 promoter, T7 promoter, lac promoter, tac promoter and EM7 promoter sequences, amongst others.

The yeast-expressible promoter may be any promoter which is capable of regulating expression of a gene at least in a yeast cell. Examples of suitable yeast-expressible promoters include the TEF1, GAL1, CUP1, SPO13, ADH2, PHO5, PRP1, GUT1 and yeast ADH1 promoter sequences, amongst others.

Derivatives of such promoters are also encompassed by the present invention. "Derivatives" of said promoters includes functional mutants, parts, fragments, homologues and analogs. Generally, said promoters may be subjected to mutagenesis to produce single or multiple nucleotides substitutions, deletions and/or additions. Nucleotide insertional derivatives of said promoters include 5' and 3' terminal fusions as well as intra-sequence insertion of single or multiple nucleotides. For example, promoters may be modified by the insertion of additional sequences to enhance or modify expression levels. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place.

The terminator may be any terminator sequence which is operable in the cells in which it is intended to be used. Examples of transcription terminators for use in yeast cells include the CYC1 and ADH terminators. The use of additional terminator sequences is not excluded.

In a particularly preferred embodiment, the first expression cassette further comprises one or more nucleotide sequences encoding a nuclear localisation motif and/or polypeptide loop, wherein said nucleotide sequences are situated within said expression cassette such that the first amino acid sequence is synthesized as an in-frame fusion polypeptide with the nuclear localisation motif and/or an epitope tag motif and/or a polypeptide loop domain.

In a particularly preferred embodiment, the nuclear localisation motif is the SV40 T-antigen nuclear localisation sequence (SV40 NLS) and the epitope tag is the V5 (V5 epitope) and the polypeptide loop is derived from thioredoxin.

In a more particularly preferred embodiment of the invention, there is provided a shuttle vector which is capable of expressing a first amino acid sequence, wherein said shuttle vector at least comprises:

(i) a first expression cassette comprising a multiple cloning site for insertion of a first nucleotide sequence which encodes said first amino acid sequence adjacent to one or more second nucleotide sequences encoding a nuclear localisation motif and/or epitope tag positioned such that a fusion polypeptide is capable of being produced between said first amino acid sequence and said nuclear localisation motif and/or epitope tag, and wherein said first and second nucleotide sequences are further operably linked to two or more tandem promoter sequences and placed upstream of a terminator sequence and wherein one of said promoter sequences is the bacterially-expressible T7 promoter and wherein one of said promoter sequences is the yeast-expressible ADH1 promoter and the terminator is ADH terminator;

(ii) a second expression cassette comprising a selectable marker gene operably linked to two or more tandem promoter sequences and placed upstream of a terminator sequence, wherein one of said promoter sequences is the bacterially-expressible EM7 promoter and wherein one of said promoter sequences is the yeast-expressible TEF1 promoter and the terminator is the CYC1 terminator;

(iii) a bacterial origin of replication; and (iv) a eukaryotic origin of replication.

More preferably, the first amino acid sequence is produced as a fusion protein with both a nuclear localisation motif and a polypeptide loop in which it is conformationally constrained.

Even more preferably or alternatively, the shuttle vector according to this embodiment of the invention comprises the features of the yeast/E.coli shuttle vector pBLOCK-1 described herein with reference to FIG. 1 or a homologue, analogue or derivative thereof. The complete nucleotide sequence of the vector pBLOCK-1 is also set forth, herein as <400>1 (SEQ ID NO: 1). The nucleotide sequence set forth in <400>1 (SEQ ID NO: 1) comprises the following features: ADH promoter within nucleotide positions 1–430, T7 promoter within nucleotide positions 431–470; translational start codon (ATG) at nucleotide positions 471–473; V5 epitope-encoding region within nucleotide positions 474–530; SV40 nuclear localisation motif-encoding region within nucleotide positions 531–557; polylinker (EcoRI-PstI) at nucleotide positions 558–616; ADH terminator commencing at nucleotide position 670; and Zeocin resistance gene commencing at nucleotide position 2864.

One such embodiment allows for the expression of a peptide library within a polypeptide loop (e.g. from the thioredoxin enzyme) cloned into the polylinker of pBlock-1 or pBlock-2 to produce a fusion protein in frame with a nuclear localization motif and epitope tag.

The shuttle vector described herein differs from previously described vectors in that it is a universal shuttle vector designed for use in multi-step cloning procedures involving host cells of more than one species.

In an alternative embodiment of this aspect of the invention, the subject shuttle vector is further modified to provide for expression in mammalian cells, by introducing into the first and second expression cassettes mammalian cell-expressible promoter and terminator sequences in tandem array with the promoter and terminator sequences already present in the subject expression cassettes. The advantage conferred by this arrangement is that clones which express desirable amino acid sequences, based on screening assays conducted in bacterial or yeast cells, may be transferred directly to mammalian bioassays. For example, its application in the method of the present invention permits the testing of peptide clones isolated from yeast host cells for biological activity in mammalian host cells without the need for a subcloning step of said peptide nucleotide sequence into a vector suitable for expression in mammalian host cells. This greatly simplifies the process of high through-put screening for blockers of deleterious cellular interactions.

Suitable mammalian cell-expressible promoter sequences include any promoter sequence which is at least capable of regulating expression in a mammalian cell. Examples of suitable promoters include the CMV promoter sequence and SV40 promoter sequence, amongst others.

Suitable mammalian cell-expressible terminator sequences include the SPA terminator sequence originally identified by Levitt et al. 1989, amongst others.

Even more preferably, the shuttle vector according to this embodiment of the invention comprises the features of the mammalian/yeast/E.coli shuttle vector pBLOCK-2 described herein with reference to FIG. 2 or a homologue, analogue or derivative thereof.

The nucleotide sequence which is inserted into the multiple cloning site of the first expression cassette may be generated by any means known to those skilled in the art, the only requirement being that it encode an amino acid sequence. In the specific embodiments of the inventive method described herein, the subject nucleotide sequence may comprise a randomly-synthesized oligonucleotide or randomly-sheared genomic DNA derived from one or more bacterial genomes. It will be apparent from the disclosure herein that random libraries may be generated by "shotgun" cloning of pools of said nucleotide sequences into the subject shuttle vector, thereby facilitating the screening of large numbers of peptide-or polypeptide encoding clones in yeast and/or bacterial cells.

In use, it is particularly preferred that the nucleotide sequence which is inserted into the multiple cloning site of the second expression cassette includes a first peptide-encoding sequence operably under the control of said promoter sequences, wherein said sequence encodes an epitope which is capable of being detected, when expressed on the surface of the cell, to facilitate the physical selection of a transfectant. According to this embodiment, only those cells which express the epitope will be capable of also expressing the cloned nucleotide sequence. Particularly preferred epitopes according to this embodiment, include, but are not limited to rat CD2 and a single-chain antibody molecule linked to a trans-membrane domain.

It is to be understood that the shuttle vector described herein is not limited in application to the method of the present invention. For example, the pBLOCK series of vectors may be used to identify an agonist or antagonist of any biological interaction in a cell, such as in the screening for compounds capable of perturbing a biological interaction that is produced according to the inventive method.

The present invention clearly extends to the use of the methods and vectors described herein to identify novel drugs, such as antibiotics or inhibitory agents. In fact, the present invention is particularly useful in drug screening protocols to identify candidate agonists and antagonists of any biological interaction. For example, bacterial expression systems may be used in high through-put screening for novel antibiotics or other inhibitory agents which target specific protein:DNA or protein:protein interactions. The pBLOCK series of vectors described herein are particularly useful in such applications, by virtue of the T7 promoter sequence contained therein which facilitates bacterial expression. In such applications, the nucleotide sequence(s) incorporated into the pBLOCK vector which are to be expressed will also carry an appropriate bacterial translation initiation sequence as described supra (see description bridging pages 20 and 21). The second nucleotide sequence may further be expressed such that the resultant peptide is constrained within the active site loop of thioredoxin or within flanking cysteine residues. As with other embodiments of the invention, the second nucleotide sequence may be synthetic and/or derived from genomic sources. Expression from the pBLOCK vector is achieved by infection of bacteria which contain the library plasmid with bacteriophage T7 or alternatively, by using publicly available strains such as *E.coli* BL21, which contain the T7 polymerase gene under lac control, because in such strains IPTG may be added to growth media to induce expression of the T7 polymerase gene. In performing this embodiment of the invention, the biological interaction is functional in the absence of the drug being screened and perturbation of that interaction is assayed in the presence of a candidate drug compound, wherein modified reporter gene expression is detected in the manner described for other embodiments of the invention.

Thus, a further aspect of the invention provides a method of identifying an antagonist of a biological interaction in a bacterial cell, said method comprising:
(i) placing the expression of a reporter molecule operably under the control of a biological interaction in said cell, wherein at least one partner of said biological interaction comprises a peptide, oligopeptide, polypeptide or protein encoded by a nucleotide sequence hat is placed operably in connection with a bacterial-expressible promoter in pBLOCK-1 or a derivative thereof;
(ii) incubating the cell in the presence of a candidate compound to be tested for the ability to antagonise the biological interaction; and
(iii) selecting cells wherein expression of said reporter molecule is modified.

Preferably, wherein the reporter molecule is lethal to the bacterial cell, expression thereof should not be allowed until the candidate compound is provided to the cell for a time and under conditions sufficient to antagonise the biological interaction leading to reporter expression. Accordingly, a preferred embodiment of the invention provides first a method of identifying an antagonist of a biological interaction in a bacterial cell, comprising:
(i) placing the expression of a cytostatic or cytotoxic reporter molecule operably under the control of a biological interaction in said cell, wherein at least one binding partner in said biological interaction comprises a peptide, oligopeptide, polypeptide or protein encoded by a nucleotide sequence that is placed operably in connection with a bacterially-expressible promoter in pBLOCK-1 or a variant thereof;
(ii) incubating the cell in the presence of a candidate compound to be tested for its ability to antagonise the biological interaction for a time and under conditions sufficient for antagonism to occur;
(iii) expressing of the binding partner under control of the bacterially-expressible promoter for a time and under conditions sufficient to result in expression of the reporter molecule in the absence of antagonism; and
(iv) selecting surviving or growing cells.

Preferably, the inducible bacterially-expressible promoter is the T7 promoter. In such circumstances, the expression of the reporter molecule may be induced by infecting cells with bacteriophage T7, which supplies the T7 polymerase function. Alternatively, the bacterial cell may be a cell which contains the T7 polymerase under lac control (e.g. *E.coli* BL21 cells), in which case the promoter may be induced by the addition of IPTG to growth medium. The candidate compound may be any small molecule, drug, antibiotic or other compound, the only requirement being that it is capable of permeating or being actively taken up by the bacterial cell or alternatively, is modified by the addition of a carrier molecule to facilitate such uptake.

In a further aspect of the invention, the peptide libraries of the present invention are employed to identify novel antibacterial peptides. According to this embodiment, there is provided a method of identifying an antibacterial peptide, comprising:
(i) transforming or transfecting a first bacterial population of cells with a peptide library described herein;
(ii) growing said first bacterial population for a time and under conditions sufficient for expression of the peptides encoded by said library to occur;
(iii) separating individual clones or pools of clones in said library into replica arrays;
(iv) lysing at least one of said replicated arrays to produce a lysate array;
(v) bringing the lysate array into physical relation with pathogenic bacteria; and
(vi) identifying those lysates that are capable of inhibiting the growth of the pathogenic bacteria, or killing the pathogenic bacteria.

For convenience, the pathogenic bacterium may be contained within a bacterial lawn on solid media, however this is not essential to the performance of this embodiment.

Preferably, the subject method further comprises the step of keying the lysate identified at step (v) back to the replicated array to localise the bacterial cell that expresses the same antibacterial peptide as that expressed in said lysate. More preferably, the genetic sequence encoding the peptide is isolated for the purposes of producing the antibacterial peptide encoded therefor.

In an exemplification of this embodiment, *Escherichia coli* BL21 lysates containing protein expressed from pBLOCK-1 peptide libraries, are assayed for their ability to inhibit the growth of pathogenic microorganisms or alternatively, for their ability to kill pathogenic microorganisms, wherein individual clones derived from a population of cells transformed or transfected with the subject peptide library are either replica-plated onto semi-permeable membranes, such as nitrocellulose or nylon membranes, or alternatively, replica-picked, to master cultures and cultures in which expression of the cloned peptide sequence is to be induced, prior to lysis. Replica-plating and/or replica-picking can be performed manually or with the assistance of robotics. Samples comprising those colonies in which expression is to be induced are lysed, for example by exposure to chloroform or by infection with a bacteriophage such as T7 bacteriophage, and overlayed on a freshly-seeded lawn of pathogenic bacteria The ability of individual peptide-expressing clones to inhibit growth or to kill the pathogenic bacterium in question is assayed by detecting the presence of a "clearing" or "hole" in the lawn of pathogenic bacteria directly beneath the position where the lysate containing the expressed antibacterial peptide occurs.

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

EXAMPLE 1

Construction of the Plasmid Vector pBLOCK-1

To construct the plasmid vector pBLOCK-1 (FIG. 1; <400>1 (SEQ ID NO: 1)), the LexA gene was removed from the plasmid pHybLex/Zeo (Invitrogen Corporation) by digestion with HindIII and re-ligation, to produce pHybLex/Zeo/ΔLexA. The T7 promoter and SV40 nuclear localisation sequence present in the plasmid pYEStrp was amplified by polymerase chain reaction (PCR) using the following primers:

1. (SEQ ID NO: 2) 5'-gagagagaagcttccccggatcgg-actactagc-3' (i.e. <400>2); and
2. (SEQ ID NO: 3) 5'-gagagagagctcgaattcagctaccttctctt-cttttttggagg-3' (i.e. <400>3).

The PCR product was digested with HindIII and Ecl136II and then cloned into the intermediate plasmid pHybLex/Zeo/ΔLexA which had been digested previously with the same enzymes, to produce pBLOCK-1.

EXAMPLE 2

Method for Identifying Inhibitors of Protein-protein Interactions

A counter-selectable reporter gene is introduced into the yeast strain used for the screen. The strain is then modified to allow the introduction of an additional plasmid expressing potential disruptors of the interaction. In one embodiment, the counter-selectable reporter gene URA3 was used to exploit the toxicity of the URA3 gene product in the presence of the drug 5-fluoroorotic acid (5FOA). Any activation of the reporter gene arising from the protein-protein interaction under study is selected against in the presence of the drug 5FOA. Yeast cells expressing peptides from the library which block the interaction will therefore be able to grow in the presence of 5FOA. In an alternative embodiment, a second counterselectable reporter gene, designated CYH2, was utilised to select yeast cells in the presence of cycloheximide. In a further embodiment, the genetic constructs utilised both the URA3 and CYH2 counterselectable reporter genes, for performing the invention in yeast cells.

As a 'bait' (DNA binding domain fusion) an existing LexA/SCL fusion protein is used which has been shown previously to interact with the DRG and E47 proteins (Mahajan, M. A. et al. (1996)). This bait contains the bHLH domain (residues 176–245) of SCL also implicated in the interaction of LMO2 (Wadman, I. (1994)). The 'prey' (activation domain fusion) constructs encode the known SCL interactors.

Screening is performed according to Vidal, M. et al. (1996), Green A. R. et al. (1991), Vidal M. et al. (1996) with the following modifications. Firstly, the pair of two hybrid interactors are based on vectors pJG4-5 and pEG202 (or pGilda) of the lex-A based two hybrid system (Gyuris, J. E. et al. (1993)). The SCL expressing LexA hybrid clone expresses residues 176–331 of SCL (Mahajan, M. A. et al. (1996)). Secondly, the reverse two hybrid aptamer library is based on the random aptamer library described by Colas et al., (23), with the exception that the vector is based on pBLOCK-1 which allows expression of peptides either alone or as fusions with other amino acids (e.g. with flanking cysteine residues). The library is transformed once and screened with the interactor pairs by mass mating (Bendixen et al. (1994). Briefly, the Zeo-marked library is introduced into strain YPH250 (Sikorski, R. S. et al. (1989)) of genotype: (MATα, leu2, ura3, lys2, trp1) and the transformants frozen. The interacting proteins encoded by plasmids marked with TRP1 and HIS4 are then transformed into a derivative of the strain YPH252 (Sikorski, R. S. et al., 1989) or strain EGY40 (Golemis and Brent, 1992; Gyuris et al., 1993) of genotype (MATα, leu2, ura3, his4, trp1, lys2) which has been transformed stably with the counter-selectable reporter constructs. Diploids yeast arising from the mating of the above two strains are selected on minimal media lacking tryptophan, and histidine but containing Zeocin and stored frozen. Screening of the library is then performed by replating on minimal media lacking leucine, tryptophan, and histidine but containing 5FOA, Zeocin and raffinose and/or galactose. In cases where the recipient strain contains the CYH2 reporter, in addition to the URA3 reporter, it is necessary for both parent strains to possess spontaneous mutations in the CYH2 gene which render the strains resistant to cycloheximide. In such instances, the counterselection media may contain cycoheximide.

The alternative bait plasmid pGilda (OriGene Corporation), rather than pEG202, in the above scheme may be preferred where the peptide, polypeptide or protein that is expressed as a LexA fusion is toxic to the cell or alternatively, possesses endogenous transcriptional activation activity sufficient to produce lethality in the counterselection screen that is independent of the relevant biological interaction being assayed. Whilst not being bound by any theory or mode of action, the improved efficacy of pGilda may be because the plasmid is maintained at a low copy number because of the presence of a CEN/ARS origin of replication rather than the 2 micron origin of replication used in many other yeast vectors. Alternatively or in addition, pGilda utilises an inducible GAL1 promoter sequence, rather than the ADH promoter sequence present on pEG202, which allows for the level of expression of the interacting protein binding partners to be regulated by the concentration of galactose in the growth medium. In particular, expression of the interacting protein binding partners from pGilda is provided for on media containing a neutral carbon source such as raffinose, in cases where expression of the interacting protein binding partners is insufficient to confer lethality, higher concentrations of galactose may be added to growth medium until sufficient quantities of the interacting proteins are expressed for the lethality associated with that interaction to be determined on counterselection plates.

EXAMPLE 3

Construction of Peptide Library

Conventional two hybrid libraries are unsuitable for the method of the present invention since, being fused to a transcriptional activation domain, they do not allow the cloning of all kinds of peptide blockers because some members of the library would activate transcription (thereby evading the screen) regardless of whether or not they block the interaction under test. Moreover, as with the vectors used in three hybrid screening (Zhang, J. et al. (1996)), it is necessary to provide an additional selectable marker in the yeast vector and to use an appropriate strain for its selection.

Presenting peptides in a constrained fashion limits the degrees of freedom, and hence the entropic cost, of binding, accounting for the high affinity of interactions observed (Colas et al. (1996)). A Trx-presented random peptide library is used in the present method. The preparation of the random inserts and Trx moiety is as described previously, (Colas et al. (1996)). The random aptamer inserts are cloned into the reverse two hybrid vector pBLOCK-1.

EXAMPLE 4

Performing the Screen for Peptide Blockers of Protein-protein Interactions

To reduce the number of yeast library transformations, a mass-mating technique to efficiently combine the library plasmids with the strains expressing the two hybrid partners issued (Bendixen, C. (1994)). After selection of diploids, and plating onto media containing 5FOA, only clones expressing blocking peptides ('blockers') form colonies since they repress the transcription of the counterselectable URA3 reporter gene. The appropriate stringency of the 5FOA negative selection is determined empirically for each interactor pair according to Vidal et al. (1996).

EXAMPLE 5

Testing Blockers for Specificity Using Interaction Mating

The 'interaction mating' (Finley Jr, R. L. et al. (1994)) technique is used to rapidly determine whether blockers isolated from the above screen are specific for the desired interaction pair. Library plasmids encoding blockers are rescued by transformation of E.coli and retransformed into the yeast. They are then each mated in parallel with a large panel of nonspecific two hybrid fusion pairs in a yeast strain of opposite mating type and tested for sensitivity to 5FOA. It is necessary that at least one of the two yeast strains contains the appropriate reporter gene(s) described above. Only clones which block specifically the interaction of SCL with its interactors and not the interaction of other similar interacting proteins, are retained for further analysis.

EXAMPLE 6

Selecting High Affinity Blockers Using Surface Plasmon Resonance

HOX11 and SCL interaction domains are purified as maltose binding protein fusions using the vector pMalC2 (New England Biolabs) and covalently coupled to the BIAcore (Pharmcia) biosensor chip. Purified GST fusions of known HOX11 and/or SCL interactors are passed over the biosensor chip and the binding monitored with a BIAcore2000 in the presence and absence of yeast extract containing over expressed Trx-aptamer blockers. In order to find the appropriate ratio for competition, each of the interactors is titrated by limiting dilution against a constant concentration of yeast extract. Blocking activity of cyclic peptides is similarly confirmed by surface plasmon resonance.

Surface plasmon resonance is suited to studying interactions of proteins identified in two hybrid screens (Colas, P. et al. (1996), Yang, M. et al. 1995). The sensitivity of the surface plasmon resonance instrument enables the identification of components of crude cell extracts which can compete with the interaction of purified proteins in solution with their cognate partners bound to a biosensor chip (Bartley, T. D. et al. (1994)). Purified SCL is immobilised by covalent coupling to the chip surface. Purified GST fusions of interactors (LMO2, DRG and E47) are then passed over the chip and the binding monitored by the BIAsensor. Yeast extracts overexpressing the much smaller peptide aptamer blockers selected in the above genetic screen or a Trx vector control polypeptide, are then passed across the chip and assessed for their ability to block association of cognate partners with SCL. If any of the peptide aptamers blocks an interaction, binding of the natural SCL partner is inhibited and a change in refractive index detected. It is this change which is measured by the BIAsensor, regardless of whether the aptamer blocker binds to SCL, to its partner or to both proteins. Since the signal is proportional to the size of the interacting protein, it is possible to detect the difference between the binding of the cognate partners of SCL and the much smaller artificial aptamer, should it interact directly with SCL. These experiments are repeated with unrelated pairs of proteins to ensure specificity. Peptide aptamers which block interactions with highest affinity and specificity are immunopurified via their Trx domain and tested for direct interactions and the dissociation constants determined prior to sequencing their inserts.

Based on the above studies, the highest affinity blockers are further examined. The inhibitory effect of peptide aptamers is initially tested by expressing them constrained within the Trx polypeptide loop in cell lines. We then synthesise the 20mer inserts corresponding to the peptide aptamers.

The 38-mer peptides are designed in the following form:

S Cys(Penetratin 16-mer)(interacting 20-mer)Cys wherein the amino acid sequence of the penetratin 16-mer motif is as described by Derossi et al, (1994): (SEQ ID NO: 4) (Arg Gln Ile Lys Ile Trp Phe Gln Asn Arg Arg Met Lys Trp Lys Lys).

The peptides (synthesised by Chiron Mimotopes, Australia) are cyclysed by oxidation of the flanking cysteine residues with 10 mM $K_3Fe(CN)_6$ (Mimotopes, Australia) at pH8.4 and purified by reverse-phase HPLC according to Koiveunen et al.(1994).

Promising candidate blocker clones are thus synthesized as cyclic peptides comprising the interacting peptide fused to the penetratin motif. This cyclisation with flanking cysteine residues is used in the design of synthetic peptides in an attempt to maintain high affinity by conformational constraint (Giebel, L. B. et al., 1995). This approach has yielded several biologically active peptide inhibitors.

EXAMPLE 7

Application of the Model System to Isolating Blockers of HOX11 Interactions

The screens are also extended to look for blockers of HOX11 interactors which are currently being isolated. In the case of HOX11, where target genes have been identified, luciferase reporter constructs containing the promoters of HOX11 targets are cotransfected with blocker constructs/peptides and the effect on growth and reporter gene expression determined. Any SCL or HOX11 specific peptides which inhibit growth are added in combination to cells as a test of synergistic cooperative inhibition of HOX11 and SCL.

EXAMPLE 8

Assays of Target Gene Activation

The promoters of HOX11 target genes are fused to the luciferase reporter pGL3 Basic Vector and expression of luciferase determined from crude extracts (Promega) in a luminometer. A plasmid cotransfection control expressing β-galactosidase is used to normalise for transfection efficiency. Peptides are added directly to fresh media at concentrations of 0.1 μM, 1 μM, 10 μM and 100 μM.

REFERENCES

1. Akiyama, et al. (1989) *Proc. Natl. Acad. Sci (USA)* 86:3949–3952.
2. Allen et al. (1995) *Trends in Biochemical Sciences* 20: 511–516.
3. Amann and Brosius (1985) *Gene* 40:183.
4. Ausubel, F. M., Brent, R., Kingston, R E, Moore, D. D., Seidman, J. G., Smith, J. A., and Struhl, K. (1987–1997) In: *Current Protocols in Molecular Biology*. Wiley Interscience (ISBN 047150338).
5. Bartley, T. D)., et al., (1994) *Nature* 368:558.
6. Bendixen, C., Gangloff, S. and Rothstein R. (1994) *Nucleic Acids Research*. 22:1778–9.
7. Chalfie, M. et al. (1994) *Science* 263:802–805.
8. Colas, P. et al. (1996) *Nature* 380:548.
9. Cormack, B. et al. (1996) *Gene* (in press).
10. Condorelli, G. L. et al. (1996) *Cancer Research* 56:5113.
11. Derossi, D. et al. (1994) *J. Biol. Chem.* 269:10444.
12. Durfee, T. K. et al. (1993) *Genes & Development* 7:555.
13. Fahraeus, E., et al. (1996) *Current Biology* 6: 84–91.
14. Fijalowska, I. J., and Schaaper, R. M. (1995) *J. Bacteriol.* 177:5979–5986.
15. Finley, Jr, R. L., et al. (1994) *Proc. Natl. Acad. Sci.* (USA) 91:12980.
16. Frick, et al. (1995) *J. Biol. Chem.* 270: 24086–24091.
17. Giebel, L. B. et al., (1995) *Biochemistry* 34:15430.
18. Golemis, E., and Brent, R. (1992) *Mol. Biol.* 12: 3006–3014.
19. Green, A. R. et al., (1991) *Oncogene* 6:475.
20. Gyuris, J. E. et al. (1993) *Cell* 75:791–803.
21. Haas, J. et al. (1996) *Curr. Biol.* 6:315–324.
22. Hsu, H. L. et al. (1991) *Mol. Cell Biol.* 11:3037.
23. Inouye, S., and Tsuji, F. I. (1994) *FEBS Letts* 341:277–280.
24. Kioveunen, E. et al. (1994) *J. Cell Biol.* 124:373.
25. Kozak, M. (1987) *Nucleic Acids Res.* 15: 8125–8148.
26. Larson, R. C. et al., (1996) *EMBO J.* 15 (5):1021.
27. Levitt, N., Briggs, D., Gil, A. and Proudfoot, N., (1989) *Genes & Devel.* 3: 1019–1025.
28. Lu, T-W., and Cillo (1995) *J. Biol. Chem.* 270:23582–23588.
29. Mahajan, M. A. et al. (1996) *Oncogene* 12:2343.
30. Maki and Sekiguchi (1992) *Nature* 355: 273–275.
31. Marcello, A. et al. (1994) *Proc. Natl. Acad. Sci. USA* 91:8994.
32. Miller, J. H. (1992) *A Short Course in Bacterial Genetics*. Cold Springs Harbor Laboratory Press, Cold Spring Harbor, N.Y.
33. Miller, J. H., and Michaels, M. (1996) *Gene* 179: 129–132.
34. Moriya and Gollman (1992) *Mol. Gen. Genetics* 239: 72–76.
35. Osada, et al. (1995) *Proc. Natl. Acad. Sci. USA* 92:9585.
36. Ow, D. W.; Wood, K. V.; DeLuca, M.; de Wet, J. R.; Helinski, D. R.; and Llowell, S. (1986) *Science* 234:856–859.
37. Prasher, D. C. et al. (1992) *Gene* 111:229–233.
38. Rabbits, T. H. (1994) *Nature* 372:143
39. Rouquet, N et al., (1996) *Current Biology* 6: 1192–1195.
40. Sambrook, J; Fritsch, E. F.; and Maniatis, T. (1989) Molecular cloning. A Laboratory Manual. Second Edition. Cold Spring Harbor Laboratory, Cold Spring Harbor, N.Y.
41. Schaaper, R. M., and Cornacchio, R. (1992) *J. Bacteriol.* 174: 1974–1982.
42. Shimatake and Rosenberg (1981) *Nature* 292:128.
43. Sikorski, R. S. et al. (1989) *Genetics*. 12219–27.
44. Slupska, M. M., et al. (1996) *Proc. Natl. Acad. Sci.* (USA) 93: 4380–4385.
45. Studier and Moffat (1986) *J. Mol. Biol.* 189:113.
46. Tajiri, et al. (1995) *Mutation Res.* 336: 257–267.
47. Thompson, J. F.; Hayes, L. S.; and Lloyd, D. B. (1991) *Gene* 103:171–177.
48. Vidal, M., P. et al. (1996) *Proc. Natl. Acad. Sci. USA* 93:10321.
49. Vidal, M. et al. (1996) *Proc. Natl. Acad. Sci. USA* 93:10315.
50. Wadman, I., J. et al. (1994) *EMBO J.* 13 (20):4831.
51. Warbrick, E., et al., (1996) *Current Biology* 5:275.
52. Yang, M. et al. (1995) *Nucleic Acid Sequence* 23 (7): 1152.
53. Zhang, J. et al. (1996) *Anal. Biochem.* 242:68.

We claim:

1. A method of identifying an inhibitory amino acid sequence that partially or completely inhibits a target protein-protein interaction or DNA-protein interaction involving one or more protein binding partners in a host cell said method comprising the steps of:
   (i) providing a cell that comprises: (a) a nucleic acid comprising a counter-selectable reporter gene encoding a polypeptide that is capable of reducing cell growth or viability by providing a target for a cytotoxic or cytostatic compound or by converting a substrate to a cytotoxic or cytostatic product, said gene being positioned downstream of a promoter comprising a cis-acting element such that expression of said gene is operably under the control of said promoter and wherein a protein binding partner of the protein-protein interaction or the DNA-protein interaction being assayed binds to said cis-acting element; and (b) nucleic acid selected from the group consisting of: (i) nucleic acid encoding a protein of the DNA-protein interaction that binds to said cis-acting element to activate expression of the counter-selectable reporter gene; and (ii) nucleic acids encoding two protein binding partners of the protein-protein interaction wherein a protein binding partner binds to the cis-acting element and the protein binding partners interact, said binding to the cis-acting element and said interaction being required to activate expression of the counter-selectable reporter gene;
   (ii) transforming or transfecting the cell with nucleic acid comprising a nucleotide sequence encoding an amino acid sequence being tested for an ability to inhibit said protein-protein interaction or DNA-protein interaction wherein expression of said nucleotide sequence is operably under the control of a promoter sequence operable in said cell;
   (iii) culturing said cell for a time and under conditions sufficient for the protein binding partner(s) to activate expression of the counter-selectable reporter gene in the absence of inhibition of the protein-protein interaction or the DNA-protein interaction by the expressed amino acid sequence being tested;
   (iv) culturing the cell under conditions sufficient for the amino acid sequence being tested to be expressed in said cell;
   (v) culturing the cell in the presence of the substrate or the cytotoxic or cytostatic compound such that the expressed counter-selectable reporter gene reduces the growth or viability of the cell unless said expression is reduced by virtue of the amino acid sequence being tested inhibiting the target protein-protein interaction or DNA-protein interaction; and
   (vi) selecting a cell having enhanced growth or viability compared to a cell that does not express the amino acid sequence being tested wherein the enhanced growth or viability is indicative of a partial or complete inhibition of the protein-protein interaction or a DNA-protein interaction by the, amino acid sequence being tested.

2. The method according to claim 1, wherein the DNA-protein interaction is between a protein and a cis-acting nucleotide sequence that modulates expression of the counter-selectable reporter and wherein the inhibitory amino acid sequence partially or completely inhibits the DNA-protein interaction sufficient to reduce or prevent expression of said counter-selectable reporter, thereby enhancing growth or viability.

3. The method according to claim 1, wherein the interaction is a protein-protein interaction between two protein binding partners.

4. The method according to claim 3, wherein one of said two protein binding partners is a DNA binding domain fusion protein comprising the DNA binding domain of a transcription factor that binds to the cis-acting element fused to an amino acid sequence that dimerises with the other of said two protein binding partners and wherein said other protein binding partner comprises a transcriptional activator domain that activates expression of the counter-selectable reporter gene and wherein dimerisation between the two proteins produces a functional transcription factor that binds to said cis-acting element and activates expression of the counter-selectable reporter gene.

5. The method according to claim 1 wherein the cis-acting element comprises a LexA operator or GAL4 recognition sequence.

6. The method according to claim 4, wherein the transcriptional activator domain is the GAL4 transcriptional activator domain.

7. The method according to claim 4, wherein the DNA binding domain fusion protein comprises an oncoprotein that interacts with said other protein binding partner or wherein the transcriptional activator domain is fused to an oncoprotein that interacts with the DNA binding domain fusion protein.

8. The method according to claim 3, wherein the protein-protein interaction further involves the interaction of an adaptor protein with said two protein binding partners.

9. The method according to claim 1, wherein providing a cell at (i) comprises introducing a nucleic acid into a cell said nucleic acid being selected from the group consisting of: (i) nucleic acid encoding a protein binding partner involved in the protein-protein or DNA-protein interaction; and (ii) nucleic acid comprising the counter-selectable reporter gene downstream of the promoter that comprises the cis-acting element.

10. The method according to claim 1 wherein the counter selectable reporter gene is selected from the group consisting of URA3, CYH2, and LYS2.

11. The method according to claim 1, wherein the amino acid sequence being tested is conformationally constrained within a Trx polypeptide loop (SEQ ID NO: 4).

12. The method according to claim 1, wherein the nucleotide sequence encoding the amino acid being tested comprises a nuclear localisation signal (NLS) capable of targeting the amino acid sequence being tested to the nucleus of the cell.

13. The method according to claim 1, wherein the promoter to which the counter-selectable reporter gene is linked is selected from the group consisting of: a MYC promoter, a GAL1 promoter, a CUP1 promoter, a PGK1 promoter, an ADH1 promoter, an ADH2 promoter, a PHO5 promoter, a PRB1 promoter, a GUT1 promoter, a SPO13 promoter, a CMV promoter, a SV40 promoter and a T7 promoter.

14. The method according to claim 1, wherein the expression of the amino acid sequence being tested is operably under the control of a promoter selected from the group consisting of: a GAL1 promoter, a CUP1 promoter, a PGK1 promoter, an ADH1 promoter, an ADH2 promoter, a PHO5 promoter, a PRB1 promoter, a GUT1 promoter, a SPO13 promoter, a CMV promoter, a SV40 promoter and a T7 promoter.

15. The method according to claim 1, wherein the nucleic acid encoding the amino acid sequence being tested is contained in a vector comprising the plasmid pBLOCK-1 (SEQ ID NO: 1) or a variant of plasmid pBLOCK-1 (SEQ ID NO: 1) comprising the nucleotide sequence of pBLOCK-1 (SEQ ID NO: 1) and a promoter and transcription terminator sequence operable in a mammalian cell for regulating expression of said amino acid sequence in a mammalian cell.

16. The method according to claim 1, wherein the cell is a yeast cell having the genotype MATα, ura3, trp1, his3, cyh2$^R$, lexAop-URA3, lexAop-CYH2, ade2.

17. The method of claim 1, wherein the inhibitory amino acid sequence is an antagonist of a target protein-protein or DNA-protein interaction in a bacterial cell and wherein the amino acid sequence being tested is expressed in said bacterial cell under the control of the T7 promoter in plasmid vector pBLOCK-1 (SEQ ID NO: 1).

18. The method of claim 1, wherein the inhibitory amino acid sequence is an antagonist of a target protein-protein or DNA-protein interaction in a bacterial cell and wherein the reporter molecule is a cytostatic or cytotoxic reporter molecule.

19. The method of claim 1 wherein the inhibitory amino acid sequence is an antibacterial peptide.

20. The method of claim 1 wherein the nucleotide sequence encoding the amino acid sequence being tested is cloned into a shuttle vector comprising two or more tandem promoter sequences for regulating expression of the amino acid sequence being tested wherein one of said promoter sequences is operable in a bacterial cell and wherein one of said promoter sequences is operable in a yeast or mammalian cell.

21. The method of claim 20, wherein said vector comprises SEQ ID NO: 1.

22. The method according to claim 1 wherein the nucleotide sequence encoding the counter-selectable reporter or the nucleotide sequence encoding the amino acid sequence being tested is operably connected to an inducible promoter such that the level of said counter-selectable reporter gene expression or the level of said amino acid sequence being tested is capable of being modulated in the cell.

23. The method of claim 22 wherein the inducible promoter is the GAL1 promoter and the level of the counter-selectable reporter or amino acid sequence being tested is modulated by varying the galactose concentration of the medium in which the cell is cultured.

24. The method of claim 22 wherein the inducible promoter is the CUP1 promoter and the level of the counter-selectable reporter or amino acid sequence being tested is modulated by varying the concentration of copper in the medium in which the cell is cultured.

25. The method of claim 1 wherein expression of a protein binding partner is operably under the control of an inducible promoter sequence such that the level of expression of said protein binding partner is capable of being modulated in the cell.

26. The method of claim 1 wherein the nucleotide sequence encoding the amino acid sequence being tested is operably connected to an inducible promoter such that the level of said amino acid sequence is capable of being modulated in the cell.

27. The method of claim 1 further comprising rescuing the nucleic acid that encodes the amino acid being tested from the cell selected at (vi).

28. The method of claim 25 wherein the inducible promoter is the GAL1 promoter.

29. The method of claim 25 wherein the inducible promoter is the CUP1 promoter.

30. A method of identifying an inhibitory amino acid sequence that partially or completely inhibits an interaction between two interacting proteins of a protein-protein interaction in a cell said method comprising:
(i) providing a cell that comprises: (a) a nucleic acid comprising a counter-selectable reporter gene downstream of a promoter that comprises a cis-acting element wherein expression of said gene is operably under the control of said promoter; (b) nucleic acid encoding an interacting protein that binds to said cis-acting element; and (c) nucleic acid encoding an interacting protein that interacts with the protein that binds the cis-acting element, wherein said nucleic acids (b) and (c) are separately and operably linked to inducible promoter sequences operable in said cell and wherein said binding to the cis-acting element and said interaction are required to activate expression of the counter-selectable reporter gene in the cell;
(ii) transforming or transfecting said cell with a vector comprising:
(a) plasmid pBLOCK-1 (SEQ ID NO: 1) or a variant of plasmid pBLOCK-1 (SEQ ID NO: 1) comprising the nucleotide sequence of pBLOCK-1 (SEQ ID NO: 1) and a promoter and transcription terminator sequence operable in a mammalian cell for regulating expression in a mammalian cell; and
(b) a nucleotide sequence placed within said plasmid or said variant and operably under the control of a promoter sequence in said plasmid or variant that is operable in said cell, wherein said sequence encodes an amino acid sequence being tested for inhibitory activity, and wherein said promoter is different from the promoters regulating expression of said interacting proteins in said cell;
(iii) culturing said cell for a time and under conditions sufficient for the interacting proteins to be expressed and to activate expression of the counter-selectable reporter gene in the absence of inhibition of the protein-protein interaction;
(iv) culturing the cell under conditions sufficient for the amino acid sequence being tested to be expressed in said cell;

(v) culturing the cell under conditions sufficient for the expressed counter-selectable reporter gene to reduce the growth or viability of the cell unless said expression is reduced by virtue of the expressed amino acid sequence being tested inhibiting the interaction between the interacting proteins; and (vi) selecting a cell having enhanced growth or viability compared to an untransformed or untransfected cell that does not express the amino acid sequence being tested wherein the enhanced growth or viability is indicative of a partial or complete inhibition of the protein-protein interaction by the amino acid sequence being tested.

31. The method of claim 30 wherein the cell is a bacterial cell.

32. The method of claim 30 wherein the cell is a mammalian cell.

33. The method of claim 30 wherein the cell is a yeast cell.

34. The method of claim 30 wherein providing a cell at (i) comprises introducing to a cell nucleic acid comprising the counter-selectable reporter gene downstream of the promoter that comprises the cis-acting element.

35. The method of claim 30 wherein providing a cell at (i) comprises introducing to a cell one or more nucleic acids encoding one or both interacting proteins wherein each of said nucleic acids is placed in operable connection with an inducible promoter sequence.

36. The method of claim 30 wherein at least one of the inducible promoters is the GAL1 promoter and wherein expression of the interacting protein is induced by the addition of galactose to the growth medium.

37. The method of claim 30 wherein at least one of the inducible promoters is the CUP1 promoter and wherein expression of the interacting protein is induced by the addition of copper to the growth medium.

38. The method of claim 30 further comprising rescuing the nucleic acid that encodes the amino acid being tested from the cell selected at (vi).

39. A method of identifying an inhibitory amino acid sequence that partially or completely inhibits an interaction between two interacting proteins of a protein-protein interaction in a cell said method comprising:

(i) providing a cell that comprises: (a) nucleic acid comprising a counter-selectable reporter gene downstream of a promoter that comprises a cis-acting element wherein expression of said gene is operably under the control of said promoter; (b) nucleic acid encoding an interacting protein that binds to said cis-acting element; and (c) nucleic acid encoding an interacting protein that interacts with the protein that binds the cis-acting element, wherein said nucleic acids (b) and (c) are separately and operably linked to promoter sequences operable in said cell and wherein said binding to the cis-acting element and said interaction are required to activate expression of the counter-selectable reporter gene in the cell;

(ii) transforming or transfecting said cell with a vector comprising:

(a) plasmid pBLOCK-1 (SEQ ID NO: 1) or a variant of plasmid pBLOCK-1 (SEQ ID NO: 1) comprising the nucleotide sequence of pBLOCK-1 (SEQ ID NO: 1) and an inducible promoter sequence and transcription terminator sequence operable in a mammalian cell for regulating expression in a mammalian cell; and (b) a nucleotide sequence placed within said plasmid or said variant and operably under the control of said inducible promoter sequence in said plasmid or variant, wherein said sequence encodes an amino acid sequence being tested for inhibitory activity, and wherein said inducible promoter is different from the promoters regulating expression of said interacting proteins in said cell;

(iii) culturing said cell for a time and under conditions sufficient for the interacting proteins to be expressed and to activate expression of the counter-selectable reporter gene in the absence of inhibition of the protein-protein interaction;

(iv) culturing the cell under conditions sufficient for the amino acid sequence being tested to be expressed in said cell;

(v) culturing the cell under conditions sufficient for the expressed counter-selectable reporter gene to reduce the growth or viability of the cell unless said expression is reduced by virtue of the expressed amino acid sequence being tested inhibiting the interaction between the interacting proteins; and (vi) selecting a cell having enhanced growth or viability compared to an untransformed or untransfected cell that does not express the amino acid sequence being tested wherein the enhanced growth or viability is indicative of a partial or complete inhibition of the protein-protein interaction by the amino acid sequence being tested.

40. The method of claim 39 wherein the cell is a bacterial cell.

41. The method of claim 39 wherein the cell is a mammalian cell.

42. The method of claim 39 wherein the cell is a yeast cell.

43. The method of claim 39 wherein providing a cell at (i) comprises introducing to the cell nucleic acid comprising the counter-selectable reporter gene downstream of the promoter that comprises the cis-acting element.

44. The method of claim 39 wherein providing a cell at (i) comprises introducing to a cell one or more nucleic acids encoding one or both interacting proteins wherein each of said nucleic acids is placed in operable connection with a promoter sequence.

45. The method of claim 39 wherein the inducible promoter is the GAL1 promoter and wherein expression of the amino acid sequence being tested is induced by the addition of galactose to the growth medium.

46. The method of claim 39 wherein at least one of the inducible promoters is the CUP1 promoter and wherein expression of the amino acid sequence being tested is induced by the addition of copper to the growth medium.

47. The method of claim 39 further comprising rescuing the nucleic acid that encodes the amino acid being tested from the cell selected at (vi).

48. A method of identifying an inhibitory amino acid sequence that partially or completely inhibits an interaction between two interacting proteins of a protein-protein interaction in a cell said method comprising:

(i) providing a cell that comprises: (a) nucleic acid comprising a counter-selectable reporter gene downstream of a promoter that comprises a cis-acting element wherein expression of said gene is operably under the control of said promoter; (b) nucleic acid encoding an interacting protein that binds to said cis-acting element; and (c) nucleic acid encoding an interacting protein that interacts with the protein that binds the cis-acting element, wherein one or both nucleic acids (b) and (c) is operably linked to an inducible promoter sequence operable in said cell and wherein said binding to the cis-acting element and said interaction are required to activate expression of the counter-selectable reporter gene in the cell;

(ii) transforming or transfecting said cell with a vector comprising:
  (a) plasmid pBLOCK-1 (SEQ ID NO: 1) or a variant of plasmid pBLOCK-1 (SEQ ID NO: 1) comprising the nucleotide sequence of pBLOCK-1 (SEQ ID NO: 1) and an inducible promoter sequence and transcription terminator sequence operable in a mammalian cell for regulating expression in a mammalian cell; and
  (b) a nucleotide sequence placed within said plasmid or said variant and operably under the control of said inducible promoter sequence in said plasmid or variant, wherein said sequence encodes an amino acid sequence being tested for inhibitory activity, and wherein said inducible promoter is different from the promoters regulating expression of said interacting proteins in said cell;

(iii) culturing said cell for a time and under conditions sufficient for the interacting proteins to be expressed and to activate expression of the counter-selectable reporter gene in the absence of inhibition of the protein-protein interaction;

(iv) culturing the cell under conditions sufficient for the amino acid sequence being tested to be expressed in said cell;

(v) culturing the cell under conditions sufficient for the expressed counter-selectable reporter gene to reduce the growth or viability of the cell unless said expression is reduced by virtue of the expressed amino acid sequence being tested inhibiting the interaction between the interacting proteins; and (vi) selecting a cell having enhanced growth or viability compared to an untransformed or untransfected cell that does not express the amino acid sequence being tested wherein the enhanced growth or viability is indicative of a partial or complete inhibition of the protein-protein interaction by the amino acid sequence being tested.

49. The method of claim 48 wherein the cell is a bacterial cell.

50. The method of claim 48 wherein the cell is a mammalian cell.

51. The method of claim 48 wherein the cell is a yeast cell.

52. The method of claim 48 wherein providing a cell at (i) comprises introducing to the cell nucleic acid comprising the counter-selectable reporter gene downstream of a promoter that comprises the cis-acting element.

53. The method of claim 48 wherein providing a cell at (i) comprises introducing to the cell one or more nucleic acids encoding one or both interacting proteins wherein each of said nucleic acids is placed in operable connection with an inducible promoter sequence.

54. The method of claim 48 wherein at least one of the inducible promoters is the GAL1 promoter and wherein expression of one or more interacting proteins or the amino acid sequence being tested is induced by the addition of galactose to the growth medium.

55. The method of claim 48 wherein at least one of the inducible promoters is the CUP1 promoter and wherein expression of one or more interacting proteins or the amino acid sequence being tested is induced by the addition of copper to the growth medium.

56. The method of claim 48 further comprising rescuing the nucleic acid that encodes the amino acid being tested from the cell selected at (vi).

57. A method of identifying an amino acid sequence that partially or completely inhibits an interaction between two interacting proteins of a protein-protein interaction in a cell said method comprising:

(i) providing a cell that comprises: (a) a nucleic acid comprising a counter-selectable reporter gene encoding a polypeptide that is capable of reducing cell growth or viability by providing a target for a cytotoxic or cytostatic compound or by converting a substrate to a cytotoxic or cytostatic product, said gene being positioned downstream of a promoter comprising a cis-acting element such that expression of said gene is operably under the control of said promoter and wherein a protein binding partner of the protein-protein interaction being assayed binds to said cis-acting element; (b) nucleic acid encoding an interacting protein that binds to said cis-acting element; and (c) nucleic acid encoding an interacting protein that interacts with the protein that binds the cis-acting element, wherein said nucleic acids (b) and (c) are separately and operably linked to inducible promoter sequences operable in said cell and wherein said binding to the cis-acting element and said interaction are required to activate expression of the counter-selectable reporter gene in the cell;

(ii) transforming or transfecting said cell with nucleic acid comprising a nucleotide sequence encoding an amino acid sequence being tested operably under the control of a promoter sequence that is operable in said cell, wherein said promoter is different from the promoters regulating expression of said interacting proteins in said cell;

(iii) culturing said cell for a time and under conditions sufficient for the interacting proteins to activate expression of the counter-selectable reporter gene in the absence of inhibition of the protein-protein interaction;

(iv) culturing the cell under conditions sufficient for the amino acid sequence being tested to be expressed in said cell;

(v) culturing the cell in the presence of the substrate or the cytotoxic or cytostatic compound such that the expressed counter-selectable reporter gene reduces the growth or viability of the cell unless said expression is reduced by virtue of the amino acid sequence being tested inhibiting the target protein-protein interaction; and (vi) selecting a cell having enhanced growth or viability compared to a cell that does not express the amino acid sequence being tested wherein the enhanced growth or viability is indicative of a partial or complete inhibition of the protein-protein interaction by the amino acid sequence being tested.

58. The method according to claim 57, wherein providing a cell at (i) comprises introducing to the cell nucleic acid comprising one or more nucleic acids encoding one or both interacting proteins wherein each of said nucleic acids is placed in operable connection with an inducible promoter sequence.

59. The method according to claim 57, wherein an inducible promoter sequence is a GAL1 promoter or a CUP1 promoter.

60. The method according to claim 59, wherein at least one of the inducible promoter sequences is the GAL1 promoter and wherein expression of the interacting proteins is induced by the addition of galactose to the growth medium.

61. The method according to claim 57, wherein one of said two proteins comprises a DNA binding domain fusion protein comprising the DNA binding domain of a transcription factor fused to an amino acid sequence that dimerises with the other of said two proteins wherein said other comprises a transcriptional activator domain and wherein dimerisation between the two proteins produces a functional transcription factor capable of binding to the cis-acting regulatory sequence and activating expression of the counter-selectable reporter gene.

62. The method according to claim 61, wherein the DNA binding domain comprises the LexA operator binding domain or a GAL4 DNA binding domain.

63. The method according to claim 61, wherein the transcriptional activator domain is the GAL4 transcriptional activator domain or the B42 transcriptional activator domain.

64. The method according to claim 61, wherein the DNA binding domain fusion protein includes an oncoprotein that interacts with said other of two said proteins, or the transcriptional activator domain is fused to an oncoprotein that interacts with said amino acid sequence.

65. The method according to claim 57, wherein the interaction between said two proteins further involves the interaction of an adaptor protein with said two proteins.

66. The method according to claim 57, wherein providing a cell at (i) comprises introducing to the cell nucleic acid comprising the counter-selectable reporter gene downstream of the promoter that comprises the cis-acting element.

67. The method according to claim 57, wherein the counter-selectable reporter gene is selected from the group consisting of URA3, CYH2, and LYS2.

68. The method of claim 57 further comprising rescuing the nucleic acid that encodes the amino acid being tested from the cell selected at (vi).

69. A method of identifying an amino acid sequence that partially or completely inhibits an interaction between two interacting proteins of a protein-protein interaction in a cell said method comprising:
(i) providing a cell that comprises: (a) nucleic acid(s) comprising two counter-selectable reporter genes each of which encodes a polypeptide that is capable of reducing cell growth or viability by providing a target for a cytotoxic or cytostatic compound or by converting a substrate to a cytotoxic or cytostatic product, each of said genes being positioned downstream of a promoter comprising a cis-acting element such that expression of said genes is operably under the control of said promoter and wherein a protein binding partner of the protein-protein interaction being assayed binds to said cis-acting element; (b) nucleic acid encoding an interacting protein that binds to said cis-acting element; and (c) nucleic acid encoding an interacting protein that interacts with the protein that binds the cis-acting element, wherein said nucleic acids (b) and (c) are separately and operably linked to promoter sequences operable in said cell and wherein said binding to the cis-acting element and said interaction are required to activate expression of the counter-selectable reporter genes in the cell;
(ii) transforming or transfecting said cell with nucleic acid comprising a nucleotide sequence encoding an amino acid sequence being tested operably under the control of a promoter sequence that is operable in said cell;
(iii) culturing said cell for a time and under conditions sufficient for the interacting proteins to activate expression of the counter-selectable reporter genes in the absence of inhibition of the protein-protein interaction;
(iv) culturing the cell under conditions sufficient for the amino acid sequence being tested to be expressed in said cell;
(v) culturing the cell in the presence of a substrate or cytotoxic or cytostatic compound such that the expressed counter-selectable reporter genes reduce the growth or viability of the cell unless said expression is reduced by virtue of the amino acid sequence being tested inhibiting the target protein-protein interaction; and
(vi) selecting a cell having enhanced growth or viability compared to a cell that does not express the amino acid sequence being tested wherein the enhanced growth or viability is indicative of a partial or complete inhibition of the protein-protein interaction by the amino acid sequence being tested.

70. The method according to claim 69, wherein providing a cell at (i) comprises introducing to the cell nucleic acids comprising the two counter-selectable reporter genes each of said genes being separately linked to promoters that comprise the cis-acting element.

71. The method according to claim 69, wherein an individual counter-selectable reporter gene is selected from the group consisting of URA3, CYH2, and LYS2.

72. The method according to claim 69, wherein one of said two interacting proteins consists of a DNA binding domain fusion protein comprising the DNA binding domain of a transcription factor fused to an amino acid sequence that dimerises with the other of said two interacting proteins and wherein the other of said two interacting proteins comprises a transcriptional activator domain and wherein dimerisation between the two interacting proteins produces a functional transcription factor that binds to the cis-acting element thereby activating expression of the counter-selectable reporter genes.

73. The method according to claim 69, wherein the cis-acting element comprises a LexA operator or a GAL4 recognition sequence.

74. The method according to claim 69, wherein one of the two interacting proteins comprises a GAL4 transcriptional activator domain or B42 transcriptional activator domain.

75. The method according to claim 69, wherein one of the two interacting proteins comprises an oncoprotein that interacts with the other of said two interacting proteins.

76. The method according to claim 69, wherein the interaction between said two interacting proteins further involves the interaction of an adaptor protein with said two interacting proteins.

77. The method according to claim 69, wherein a promoter sequence regulating expression of an interacting protein is an inducible promoter.

78. The method according to claim 69, wherein providing a cell at (i) comprises introducing to the cell one or more nucleic acids encoding one or both interacting proteins wherein each of said nucleic acids are placed in operable connection with an inducible promoter sequence.

79. The method according to claim 77, wherein an inducible promoter is a GAL1 promoter or a CUP1 promoter.

80. The method according to claim 79, wherein an inducible promoter sequence is the GAL1 promoter and wherein expression of an interacting protein under the control of said GAL1 promoter is induced by the addition of galactose to the growth medium.

81. The method according to claim 77, wherein the level of expression of the interacting proteins is altered by modulating the concentration of galactose in the growth medium.

82. The method according to claim 69, wherein sequence regulating expression of the amino acid sequence being tested is different from the promoter(s) regulating expression of the interacting proteins in said cell.

83. The method of claim 69, further comprising rescuing the nucleic acid that encodes the amino acid being tested from the cell selected at (vi).

84. A method of identifying an amino acid sequence that partially or completely inhibits an interaction between two interacting proteins of a protein-protein interaction in a yeast cell said method comprising:

(i) providing a yeast cell that comprises: (a) nucleic acid comprising the counter-selectable reporter gene URA3 linked to a promoter that comprises a cis-acting element such that expression of said gene is operably under the control of said promoter; (b) nucleic acid comprising the counter-selectable reporter gene CYH2 linked to a promoter that comprises the cis-acting element such that expression of said gene is operably under the control of said promoter; (c) nucleic acid encoding a fusion protein that comprises an interacting protein selected from the group consisting of SCL, E47 and LMO2 and a DNA binding domain that binds to said cis-acting element at (a) and (b); and (d) nucleic acid encoding a fusion protein that comprises an amino acid sequence that binds to the interacting protein at (c) and a transcription activation domain sequence, wherein said nucleic acids (c) and (d) are each separately and operably linked to a promoter sequence operable in said cell and wherein said binding to the cis-acting element and said interaction are required to activate expression of the counter-selectable reporter genes URA3 and CYH2 in the cell;

(ii) transforming or transfecting said yeast cell with nucleic acid comprising a nucleotide sequence encoding an amino acid sequence being tested operably under the control of a promoter sequence that is operable in said cell;

(iii) culturing said cell for a time and under conditions sufficient for the interacting proteins to activate expression of the counter-selectable reporter genes in the absence of inhibition of the protein-protein interaction;

(iv) culturing the cell under conditions sufficient for the amino acid sequence being tested to be expressed in said cell;

(v) culturing the cell in the presence of cycloheximide and 5-fluoro-orotic acid such that expression of the counter-selectable reporter genes reduces the growth or viability of the cell unless said expression is reduced by virtue of the expressed amino acid sequence being tested inhibiting the interaction between the interacting proteins; and (vi) selecting a cell having enhanced growth or viability compared to a cell that does not express the amino acid sequence being tested wherein the enhanced growth or viability is indicative of a partial or complete inhibition of the protein-protein interaction by the amino acid sequence being tested.

85. The method of claim 84 further comprising rescuing the nucleic acid that encodes the amino acid being tested from the cell selected at (vi).

* * * * *

UNITED STATES PATENT AND TRADEMARK OFFICE
CERTIFICATE OF CORRECTION

PATENT NO. : 6,610,495 B1
DATED : August 26, 2003
INVENTOR(S) : Watt et al.

Page 1 of 1

It is certified that error appears in the above-identified patent and that said Letters Patent is hereby corrected as shown below:

Drawings,
Figure 1, please delete "pBLOCK-2" and replace with -- pBLOCK-1 --. (as shown below)

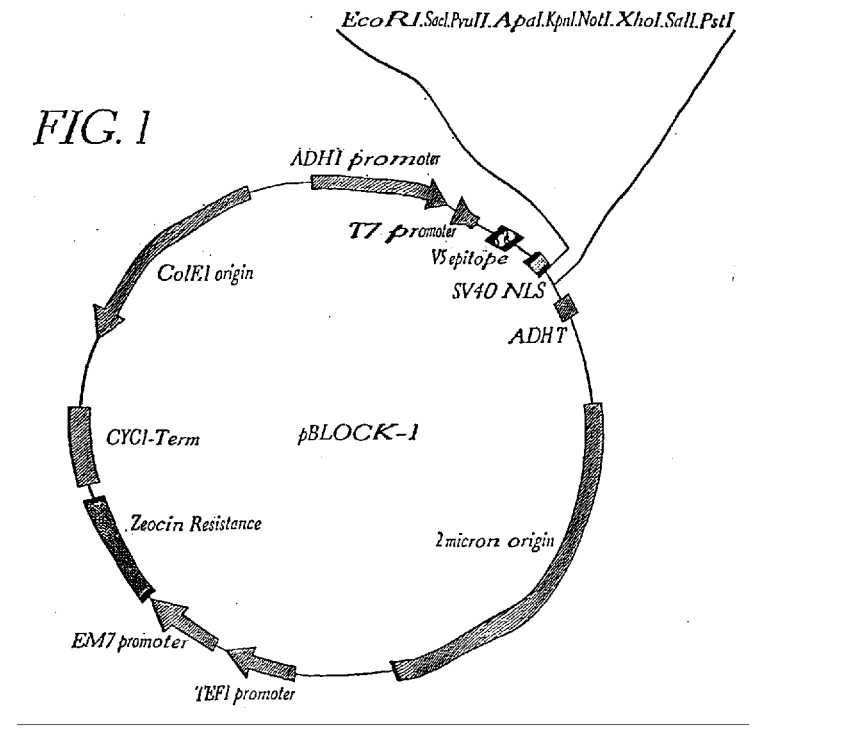

Signed and Sealed this

Twenty-fourth Day of August, 2004

JON W. DUDAS
*Director of the United States Patent and Trademark Office*

SEQUENCE LISTING

<160> NUMBER OF SEQ ID NOS: 4

<210> SEQ ID NO 1
<211> LENGTH: 4291
<212> TYPE: DNA
<213> ORGANISM: Artificial Sequence
<220> FEATURE:
<223> OTHER INFORMATION: Description of Artificial Sequence:VECTOR

<400> SEQUENCE: 1

```
caacttcttt tcttttttt tcttttctct ctcccccgtt gttgtctcac catatccgca      60
atgacaaaaa aaatgatgga agacactaaa ggaaaaaatt aacgacaaag acagcaccaa     120
cagatgtcgt tgttccagag ctgatgaggg gtatcttcga acacacgaaa cttttccctt     180
ccttcattca cgcacactac tctctaatga gcaacggtat acggccttcc ttccagttac     240
ttgaatttga aataaaaaaa gtttgccgct ttgctatcaa gtataaatag acctgcaatt     300
attaatcttt tgtttcctcg tcattgttct cgttcccttt cttccttgtt tcttttctg      360
```

-continued

```
cacaatattt caagctatac caagcataca atcaactcca agcttcccg gatcggacta       420
ctagcagctg taatacgact cactataggg aatattaagc taagctcacc atgggtaagc      480
ctatccctaa ccctctcctc ggtctcgatt ctacacaagc tatgggtgct cctccaaaaa      540
agaagagaaa ggtagctgaa ttcgagctca gatctcagct gggcccggta ccgcggccgc      600
tcgagtcgac ctgcagccaa gctaattccg ggcgaatttc ttatgattta tgattttttat    660
tattaaataa gttataaaaa aataagtgt atacaaattt taaagtgact cttaggtttt      720
aaaacgaaaa ttcttgttct tgagtaactc tttcctgtag gtcaggttgc tttctcaggt      780
atagcatgag gtcgctctta ttgaccacac ctctaccggc atgccgagca aatgcctgca      840
aatcgctccc catttcaccc aattgtagat atgctaactc cagcaatgag ttgatgaatc      900
tcggtgtgta ttttatgtcc tcagaggaca ataccctgttg taatccgtcc caagctaacg     960
aagcatctgt gcttcatttt gtagaacaaa atgcaacgc gagagcgcta attttttcaaa    1020
caaagaatct gagctgcatt tttacagaac agaaatgcaa cgcgaaagcg ctattttacc   1080
aacgaagaat ctgtgcttca tttttgtaaa acaaaaatgc aacgcgagag cgctaatttt    1140
tcaaacaaag aatctgagct gcatttttac agaacagaaa tgcaacgcga gagcgctatt   1200
ttaccaacaa agaatctata cttcttttttt gttctacaaa aatgcatccc gagagcgcta    1260
tttttctaac aaagcatctt agattacttt ttttctcctt tgtgcgctct ataatgcagt   1320
ctcttgataa cttttttgcac tgtaggtccg ttaaggttag aagaaggcta ctttggtgtc    1380
tattttctct tccataaaaa aagcctgact ccacttcccg cgtttactga ttactagcga    1440
agctgcgggt gcattttttc aagataaagg catcccgat tatattctat accgatgtgg    1500
attgcgcata ctttgtgaac agaaagtgat agcgttgatg attcttcatt ggtcagaaaa    1560
ttatgaacgg tttcttctat tttgtctcta tatactacgt ataggaaatg tttacatttt    1620
cgtattgttt tcgattcact ctatgaatag ttcttactac aattttttg tctaaagagt     1680
aatactagag ataaacataa aaatgtaga ggtcgagttt agatgcaagt tcaaggagcg     1740
aaaggtggat gggtaggtta tagggata tagcacagag atatatagca aagagatact      1800
tttgagcaat gtttgtggaa gcggtattcg caatatttta gtagctcgtt acagtccggt    1860
gcgttttttgg tttttttgaaa gtgcgtcttc agagcgcttt tggttttcaa aagcgctctg   1920
aagttcctat actttctagc tagagaatag gaacttcgga ataggaactt caaagcgttt    1980
ccgaaaacga gcgcttccga aaatgcaacg cgagctgcgc acatacagct cactgttcac    2040
gtcgcaccta tatctgcgtg ttgcctgtat atatatatac atgagaagaa cggcatagtg    2100
cgtgtttatg cttaaatgcg ttatggtgca ctctcagtac aatctgctct gatgccgcat    2160
agttaagcca gccccgacac ccgccaacac ccgctgacgc gccctgacgg gcttgtctgc    2220
tcccggcatc cgcttacaga caagctgtga ccgtctccgg gagctgcatg tgtcagaggt    2280
tttcaccgtc atcaccgaaa cgcgcgagac gaaagggcct cgtgatacgc ctatttttat    2340
aggttaatgt catgataata atggtttctt aggggatcc cccacacacc atagcttcaa     2400
aatgtttcta ctcctttttt actcttccag attttctcgg actccgcgca tcgccgtacc    2460
acttcaaaac acccaagcac agcatactaa attttccctc tttcttcctc tagggtgtcg    2520
ttaattaccc gtactaaagg tttggaaaag aaaaagaga ccgcctcgtt tcttttttctt    2580
cgtcgaaaaa ggcaataaaa attttttatca cgtttctttt tcttgaaatt ttttttttta   2640
gtttttttct ctttcagtga cctccattga tatttaagtt aataaacggt cttcaatttc    2700
tcaagtttca gtttcatttt tcttgttcta ttacaacttt ttttacttct tgttcattag    2760
```

```
aaagaaagca tagcaatcta atctaagggg cggtgttgac aattaatcat cggcatagta      2820
tatcggcata gtataatacg acaaggtgag gaactaaacc atggccaagt tgaccagtgc      2880
cgttccggtg ctcaccgcgc gcgacgtcgc cggagcggtc gagttctgga ccgaccggct      2940 cggggttctcc cggacttcg tgaggacga cttcgccggt gtggtccggg acgacgtgac       3000
cctgttcatc agcgcggtcc aggaccaggt ggtgccggac aacaccctgg cctgggtgtg      3060
ggtgcgcggc ctggacgagc tgtacgccga gtggtcggag gtcgtgtcca cgaacttccg      3120
ggacgcctcc gggccggcca tgaccgagat cggcgagcag ccgtggggc gggagttcgc       3180 cctgcgcgac ccggccggca actgcgtgca cttcgtggcc gaggagcagg actgacacgt      3240
ccgacggcgg cccacgggtc ccaggcctcg gagatccgtc cccctttttcc tttgtcgata    3300 tcatgtaatt agttatgtca cgcttacatt cacgccctcc ccccacatcc gctctaaccg      3360
aaaaggaagg agttagacaa cctgaagtct aggtccctat ttattttttt atagttatgt     3420
tagtattaag aacgttattt atatttcaaa tttttctttt ttttctgtac agacgcgtgt     3480
acgcatgtaa cattatactg aaaaccttgc ttgagaaggt tttgggacgc tcgaaggctt     3540
taatttgcaa gctggagacc aacatgtgag caaaaggcca gcaaaaggcc aggaaccgta     3600 aaaggccgc gttgctggcg ttttccata ggctccgccc ccctgacgag catcacaaaa       3660
atcgacgctc aagtcagagg tggcgaaacc cgacaggact ataaagatac caggcgtttc     3720
cccctggaag ctccctcgtg cgctctcctg ttccgaccct gccgcttacc ggatacctgt     3780
ccgcctttct cccttcggga agcgtggcgc tttctcaatg ctcacgctgt aggtatctca     3840
gttcggtgta ggtcgttcgc tccaagctgg gctgtgtgca cgaaccccc gttcagcccg      3900 accgctgcgc cttatccggt aactatcgtc ttgagtccaa cccggtaaga cacgacttat     3960
cgccactggc agcagccact ggtaacagga ttagcagagc gaggtatgta ggcggtgcta     4020
cagagttctt gaagtggtgg cctaactacg gctacactag aaggacagta tttggtatct    4080
gcgctctgct gaagccagtt accttcggaa aaagagttgg tagctcttga tccggcaaac     4140
aaaccaccgc tggtagcggt ggtttttttg tttgcaagca gcagattacg cgcagaaaaa     4200
aaggatctca agaagatcct ttgatctttt ctacggggtc tgacgctcag tggaacgaaa     4260
actcacgtta agggattttg gtcatgagat c                                    4291
```

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 2
gagagagaag cttccccgga tcggactact agc                                   33

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 3
gagagagagc tcgaattcag ctacctttct cttcttttt ggagg                       45

<210> SEQ ID NO 4

```
-continued

<211> LENGTH: 16
<212> TYPE: PRT
<213> ORGANISM: Artificial Sequence
<220> FEATURE:
<223> OTHER INFORMATION: Description of Artificial Sequence:
      Penetratin 16-mer.

<400> SEQUENCE: 4

Arg Gln Ile Lys Ile Trp Phe Gln Asn Arg Arg Met Lys Trp Lys
 1               5                  10                  15

Lys
```